US007678893B2

(12) United States Patent
Barsova et al.

(10) Patent No.: US 7,678,893 B2
(45) Date of Patent: Mar. 16, 2010

(54) **FLUORESCENT PROTEINS FROM *COPEPODA* SPECIES AND METHODS FOR USING SAME**

(75) Inventors: Ekaterina Vladimirovna Barsova, Moscow (RU); Sergei Anatolievich Lukyanov, Moscow (RU)

(73) Assignee: Zakrytoe Aktsionernoe Obschestvo "Evrogen", Moscow (RU)

( * ) Notice: Subject to any disclaimer, the term of this patent is extended or adjusted under 35 U.S.C. 154(b) by 715 days.

(21) Appl. No.: 10/533,781

(22) PCT Filed: Nov. 26, 2003

(86) PCT No.: PCT/RU03/00525

§ 371 (c)(1),
(2), (4) Date: Oct. 19, 2005

(87) PCT Pub. No.: WO2004/058973

PCT Pub. Date: Jul. 15, 2004

(65) Prior Publication Data

US 2008/0104721 A1    May 1, 2008

(51) Int. Cl.
*C07H 21/02* (2006.01)
*C12N 5/00* (2006.01)
*C12N 5/02* (2006.01)

(52) U.S. Cl. .................... 536/23.1; 435/325
(58) Field of Classification Search ............. 536/23.1
See application file for complete search history.

(56) References Cited

U.S. PATENT DOCUMENTS

| | | | |
|---|---|---|---|
| 5,182,202 A | 1/1993 | Kajiyama et al. |
| 5,221,623 A | 6/1993 | Legocki et al. |
| 5,229,285 A | 7/1993 | Kajiyama et al. |
| 5,330,906 A | 7/1994 | Kajiyama et al. |
| 5,418,155 A | 5/1995 | Cormier et al. |
| 5,439,797 A | 8/1995 | Tsien et al. |
| 5,491,084 A | 2/1996 | Chalfie et al. |
| 5,618,722 A | 4/1997 | Zenno et al. |
| 5,650,135 A | 7/1997 | Contag et al. |
| 5,674,713 A | 10/1997 | McElroy et al. |
| 5,688,648 A | 11/1997 | Mathies et al. |
| 5,700,673 A | 12/1997 | McElroy et al. |
| 5,707,804 A | 1/1998 | Mathies et al. |
| 5,728,528 A | 3/1998 | Mathies et al. |
| 5,795,737 A | 8/1998 | Seed et al. |
| 5,824,485 A | 10/1998 | Thompson et al. |
| 5,843,746 A | 12/1998 | Tatsumi et al. |
| 5,863,727 A | 1/1999 | Lee et al. |
| 5,866,336 A | 2/1999 | Nazarenko et al. |
| 5,869,255 A | 2/1999 | Mathies et al. |
| 5,874,304 A | 2/1999 | Zolotukhin et al. |
| 5,911,952 A | 6/1999 | Tsuji |
| 5,919,445 A | 7/1999 | Chao |
| 5,945,283 A | 8/1999 | Kwok et al. |
| 5,945,526 A | 8/1999 | Lee et al. |
| 5,958,713 A | 9/1999 | Thastrup et al. |
| 5,968,738 A | 10/1999 | Anderson et al. |
| 5,968,750 A | 10/1999 | Zolotukhin et al. |
| 5,972,638 A | 10/1999 | Burlage et al. |
| 5,976,796 A | 11/1999 | Szalay et al. |
| 5,981,200 A | 11/1999 | Tsien et al. |
| 5,985,577 A | 11/1999 | Bulinski |
| 5,989,835 A | 11/1999 | Dunlay et al. |
| 5,998,146 A | 12/1999 | Latva et al. |
| 6,008,373 A | 12/1999 | Waggoner et al. |
| 6,020,192 A | 2/2000 | Muzyczka et al. |
| 6,066,476 A | 5/2000 | Tsien et al. |
| 6,130,313 A | 10/2000 | Li et al. |
| 6,232,107 B1 | 5/2001 | Bryan et al. |
| 6,486,382 B1 | 11/2002 | Gordan-Kamm et al. |
| 7,157,566 B2 * | 1/2007 | Tsien et al. ............. 536/23.1 |

FOREIGN PATENT DOCUMENTS

| | | |
|---|---|---|
| JP | 10-234382 | 9/1998 |
| WO | WO 99/37142 | 7/1999 |
| WO | 00/02997 | 1/2000 |
| WO | 00/03246 | 1/2000 |

(Continued)

OTHER PUBLICATIONS

Godwin, 1998, PNAS, vol. 95, pp. 13042-13047.*
Chiu TL et al., Optimizing energy potentials for success in protein tertiary structure prediction, Folding and Design, 1998, 3:223-228.*
Wallace et al., Methods Enzymol, vol. 152, pp. 432-443, 1987.*
Sambrook et al., Molecular Cloning, 2nd Edition, 1989, Cold Spring Harbor Laboratory, Cold Spring Harbor, NY, p. 11.47.*
Pekarsky, Y et al, 1998, PNAS, 95:8744-8749.*

(Continued)

*Primary Examiner*—Valarie Bertoglio
(74) *Attorney, Agent, or Firm*—Bret E. Field; Bozicevic, Field & Francis LLP

(57) ABSTRACT

The present invention provides nucleic acid molecules encoding a fluorescent and proteins and mutants, homologues and derivatives thereof, as well as proteins and peptides encoded by these nucleic acids. The nucleic acid molecules and proteins of interest are isolated from *Copepoda* species. Also of interest are proteins that are substantially similar to, or derivatives, or homologues, or mutants of, the above-referenced specific proteins. Also provided are fragments of the nucleic acids and the peptides encoded thereby, as well as antibodies specific to the proteins and peptides of the invention. In addition, host-cells, stable cell lines and transgenic organisms comprising above-referenced nucleic acid molecules are provided. The subject protein and nucleic acid compositions find use in a variety of different applications and methods, particularly for labeling of biomolecules, cell or cell organelles. Finally, kits for use in such methods and applications are provided.

11 Claims, 5 Drawing Sheets

FOREIGN PATENT DOCUMENTS

| WO | 00/17624 | 3/2000 |
| --- | --- | --- |
| WO | 00/17643 | 3/2000 |
| WO | 00/26408 | 5/2000 |
| WO | 00/34318 | 6/2000 |
| WO | 01/27150 | 4/2001 |
| WO | 02/059309 | 8/2002 |
| WO | 03/062270 | 7/2003 |

OTHER PUBLICATIONS

Alignment of nucleotides 4084-4099 GenBank Acc. No.AF069985, US National Library of Medicine, Bethesda, MD, with nucleotides 3-18 of SEQ ID No. 3, accessed by PTO on Oct. 2, 2008.*

Kennell, DE, 1971, Progr Nucl. Acid Res. Mol. Biol., 11:259-301.*

AAN52735. Green Fluorescent Protein as (s) FP499 [*Anemonia sulcata*] dated Oct. 24, 2002 SEQ N9:24306649.

Patent Abstracts of Japan and English Computer-Generated Translation of JP 10-234382 dated Sep. 8, 1998.

Lippincott-Schwarts, et al. "Development and Use of Fluorescent Protein Markers in Living Cells." *Science* (2003) vol. 300, pp. 87-91.

PubMed Abstract. Chalfie, M., et al. "Green Fluorescent Protein as a Marker for Gene Expression." *Science* (1994) vol. 263 (5148), pp. 802-805.

Heim, R., et al. "Wavelength Mutations and Posttranslational Autoxidation of Green fluorescent *Protein*." *Proc. Natl. Acad. Sci. USA* (1994) Vo. 91, pp. 12501-12504.

PubMed Abstract. Rizzuto, R., et al. "Chimeric Green Fluorescent Protein as a Tool for Visualizing Subcellular Organelles in Living Cells." *Curr. Biol.* (1995) vol. 5 (6) pp. 635-642.

PubMed Abstract. Kaether, C., et al. "Visualization of Protein Transport Along the Secretory Pathway Using Green Fluorescent Protein." *Febs. Lett.* (1995) vol. 369 (2-3) pp. 267-271.

PubMed Abstract. Haas, J., et al. "Codon Usage Limitation in the Expression of HIV-1 Envelope Glycoprotein." *Curr. Biol.* (1996) vol. 6(3) pp. 315-324.

Yang, T., et al. "Optimized Codon Usage and Chromophore Mutations Provide Enhanced Sensitivity with the Green Fluorescent Protein." *Nucl. Acids Res.* (1996) 24, pp. 4592-4594.

Matz, M., et al. "Fluorescent Proteins from Nonbioluminescent *Anthozoa* Species." *Nature Biotechnology* (1999) vol. 17, pp. 969-973.

Matz, M., et al. "Family of the Green Fluorescent Protein: Jorney to the End of the Rainbow." *Bioessays* (2002) vol. 24, No. 10, pp. 953-959.

Xia, N., et al. "Bioluminescence of *Aequorea macrodactyla*, a Common Jellyfish Species in the East China Sea." *Marine Biotechnology* (2002) vol. 4, pp. 155-162.

Gurskaya, N., et al. "A Colourless Green Fluorescent Protein Homologue from the Non-Fluorescent Hydromedusa *Aequorea coerulescens* and Its Fluorescent Mutants." *Biochem. J.* (2003) 373, pp. 403-408.

* cited by examiner

```
                    10         20         30         40         50
GFP        MSKGEELFTGVVPILVELDGDVNGHKFSVSGEGEGDATYGKLTLKFICTTGKLPVP..WPT  SEQ ID NO:29
DsRed      MRSSKNVIKEFMRFKVRMEGTVNGHEFEIEGEGEGRPYEGHNTVKLKVTKGG.PLPFAWDI  SEQ ID NO:30
ppluGFP1       MPAMKIECRISGTLNGVVFELVGGGEGIPEQGRMTNKMKSTKGA,.LTFSPYL  SEQ ID NO:02
ppluGFP2       -----------T-----E-----------T--------------,.-------  SEQ ID NO:04
laesGFP        --V----------M--EE-----A-D-NTDE-------------..P-S----  SEQ ID NO:06
pmeaGFP1       --D--L--H----M--EE---I-A-D-NTDE---------I--..PIS-----  SEQ ID NO:08
pmeaGFP2       --D--L--H----M--EE---I-S-D-NTD------N---I--..P-S-----  SEQ ID NO:10
pmedGFP1       --N--L-------M--EE-----A---NTDE-------------..P-S-----  SEQ ID NO:12
pmedGFP2       --H--L-------M--EE-----A-D-NTDE-----Q-------..P-S-----  SEQ ID NO:14
pdaelGFP       -A---------T--M---E---------NTD-------------..P-S-----  SEQ ID NO:16

60         70         80         90        100        110
GFP        LVTTFSYGVQCFSRYPDHMKQHDFFKSAMPEGYVQERTIFFKDDGNYKTRAEVKFEGDT  SEQ ID NO:29
DsRed      LSPQFQYGSKVYVKHPADIP..DYKKLSFPEGFKWERVMNFEDGGVVTVTQDSSLQDGC  SEQ ID NO:30
ppluGFP1   LSHVMGYGFYHFGTYPSGYEN.PFLHAINNGGYTNTRIEKYEDGGVLHVSFSYRYEAGR  SEQ ID NO:02
ppluGFP2   ------------------------I---------------------------------  SEQ ID NO:04
laesGFP    ---I-------YA-F-A----.VY----K----------T-R-----IIS-N-T---GNK  SEQ ID NO:06
pmeaGFP1   ---IL---Y---A-F-A----.IY---MK----S-V-T-R-----IISIT-N----GNK  SEQ ID NO:08
pmeaGFP2   ---IL---Y---A-F-A----.IY---MK----S-V-T-R-----IISIT-N----GSK  SEQ ID NO:10
pmedGFP1   ----L---Y--YA-F-A----.VY---MK----S---T-R-----IISAT-N----GRQ  SEQ ID NO:12
pmedGFP2   ----L---Y--YA-F-A----.VY---MK----S---T-R-D---IISAT-N----GRQ  SEQ ID NO:14
pdaelGFP   --------------F------.-YV--MT----------S-------YLT-N--LDGNK  SEQ ID NO:16

120        130        140        150        160        170
GFP        LVNRIELKGIDFKEDGNILGHKLEYNYNSHNVYIMADKQKNGIKVNFKIRHNIEDGSVQL  SEQ ID NO:29
DsRed      PIYKVKFIGVNFPSDGPVMQ.KKTMGWEASTERLYP..RDGVLKGEIHKALKLKDGGHYL  SEQ ID NO:30
ppluGFP1   VIGDFKVVGTGFPEDS.VIFTDKIIRSNATVEHLHP.MGDNVLVGSFARTFSLRDGGYYS  SEQ ID NO:02
ppluGFP2   ---------------,-----------------,--------------------------  SEQ ID NO:04
laesGFP    ---------S---AN-,--------K--P-C--IY-.K---I---NAYT--WM-------  SEQ ID NO:06
pmeaGFP1   I---------TN--,L--------K--P-C-NMF-.KA--T--NAYT--YL-K------  SEQ ID NO:08
pmeaGFP2   I-------I---T--,L--------K--P-C-NMF-.KA--I--NAYT--YL-K------  SEQ ID NO:10
pmedGFP1   IH---------A--,X--------K--P-C--IY-.KAN-I--NAYT--WM--------  SEQ ID NO:12
pmedGFP2   IH---------A--,Y--------K--P-C--IY-.KAD-I--NAYT--WM--------  SEQ ID NO:14
pdaelGFP   I----C---------.--------K--PNC--FY-..AE-IMKNAYM--L---------  SEQ ID NO:16

180        190        200        210        220        230
GFP        ADHYQQNTPIGDG.PVLLPDNHYLSTQSALSKDPNEKRDHMVLLEFVTAAGITHGMDELYK  SEQ ID NO:29
DsRed      VEFKSIYMAKK...PVQLPGYYVDSKLDITSHNEDYT.IVEQYERTEGRHHLFL         SEQ ID NO:30
ppluGFP1   FVVDSHMHFKSAIHPSILQNGGSMFAFRRVEELHSNT..ELGIVEYQHAFKTPTAFA     SEQ ID NO:02
ppluGFP2   ----------------P---------------,--------------I---           SEQ ID NO:04
laesGFP    AQ-NN-L--T-M--TM--------TY-K------QS..DV--------V--------    SEQ ID NO:06
pmeaGFP1   AQ-NN--------TTM--------TY-V---T-TQN..-VA-----NV--------     SEQ ID NO:08
pmeaGFP2   AQ-NN--------TM---------TH-V---N-TK-..NVA-----NV--------     SEQ ID NO:10
pmedGFP1   AQ-NN---LQ----TM-K------TY-K-----TQ-...-V------V---R----    SEQ ID NO:12
pmedGFP2   AQ-NN---FK----TM--------TY-K-----TQ-...-V------V---R----    SEQ ID NO:14
pdaelGFP   GQ-T--I---N-------H------TY-------TQ-...D-------V--------   SEQ ID NO:16
```

FIG. 1

FLUORESCENT PROTEINS FROM *COPEPODA* SPECIES AND METHODS FOR USING SAME

FIELD OF THE INVENTION

This invention relates generally to the field of biology and chemistry. More particularly, the invention is directed to fluorescent proteins.

BACKGROUND OF THE INVENTION

Labeling of a protein, cell, or organism of interest plays a prominent role in many biochemical, molecular biological and medical diagnostic applications. A variety of different labels have been developed and used in the art, including radiolabels, chromolabels, fluorescent labels, chemiluminescent labels, and the like, with varying properties and optimal uses. However, there is continued interest in the development of new labels. Of particular interest is the development of new protein labels, including fluorescent protein labels. Fluorescent proteins or fluoroprotein are proteins that exhibit low, medium or intense fluorescence upon irradiation with light of the appropriate excitation wavelength. The fluorescent characteristic of these proteins is one that arises from the interaction of two or more amino acid residues of the protein, and not from a single amino acid residue. As such, the fluorescent proteins do not include proteins that exhibit fluorescence only from residues that act by themselves as intrinsic fluors, i.e., tryptophan, tyrosine and phenylalanine. As used herein, the term "fluorescent protein" does not include luciferases, such as Renilla luciferase.

Green Fluorescent Protein (GFP), its mutants and homologs are widely known today due to their intensive use as in vivo fluorescent markers in biomedical sciences discussed in detail by Lippincott-Schwartz and Patterson in Science (2003) 300(5616):87-91). The GFP from hydromedusa *Aequorea aequorea* (synonym *A. victoria*), discovered by Johnson et al. in J Cell Comp Physiol. (1962), 60:85-104, was found as a part of bioluminescent system of the jellyfish where GFP played role of a secondary emitter transforming blue light from photoprotein aequorin into green light cDNA encoding *A. victoria* GFP was cloned by Prasher et al. (Gene (1992), 111(2):229-33). It turned out, that this gene can be heterologically expressed in practically any organism due to unique ability of GFP to form fluorophore by itself (Chalfie et al., Science 263 (1994), 802-805). This finding opens broad perspectives for use of GFP in cell biology as a genetically encoded fluorescent label.

The GFP was applied for wide range of applications including the study of gene expression and protein localization (Chalfie et al., Science 263 (1994), 802-805, and Heim et al. in Proc. Nat. Acad. Sci. (1994), 91: 12501-12504), as a tool for visualizing subcellular organelles in cells (Rizzuto et al., Curr. Biology (1995), 5: 635-642), for the visualization of protein transport along the secretory pathway (Kaether and Gerdes, FEBS Letters (1995), 369: 267-271).

A great deal of research is being performed to improve the properties of GFP and to produce GFP reagents useful and optimized for a variety of research purposes. New versions of GFP have been developed, such as a "humanized" GFP DNA, the protein product of which has increased synthesis in mammalian cells (Haas, et al., Current Biology (1996), 6: 315-324; Yang, et al., Nucleic Acids Research (1996), 24: 4592-4593). One such humanized protein is "enhanced green fluorescent protein" (EGFP) mutant variant of GFP having two amino acid substitutions: F64L and S65T (Heim et al., Nature 373 (1995), 663-664). Other mutations to GFP have resulted in blue-, cyan- and yellow-green light emitting versions.

Despite the great utility of GFP, however, other fluorescent proteins with properties similar to or different from GFP would be useful in the art. In particular, benefits of novel fluorescent proteins include fluorescence resonance energy transfer (FRET) possibilities based on new spectra and better suitability for larger excitation. In 1999, GFP homologs were cloned from non-bioluminescent *Anthozoa* species (Matz et al., Nature Biotechnol. (1999), 17: 969-973). This discovery demonstrated that these proteins are not necessary component of bioluminescence machinery. *Anthozoa*-derived GFP-like proteins showed great spectral diversity including cyan, green, yellow, red fluorescent proteins and purple-blue non-fluorescent chromoproteins (CPs) (Matz et al., Bioessays (2002), 24(10):953-959). Afterwards, cDNA of GFP homologs were cloned from several Hydroid medusae, including *Aequorea macrodactyla* (GenBank accession numbers AF435427-AF435433) and *Aequorea coerulescens* (Gurskaya et al., Biochem J. (2003), 373(Pt 2): 403-408). Thus far, the 40-years history of GFP research revealed GFP-like proteins only within two Cnidaria classes Hydrozoa and Anthozoa.

The utility of fluorescent proteins as a tool in molecular biology has prompted the search for other fluorescent proteins with different and improved properties, as compared to known fluorescent proteins. Thus, it is an object to provide novel fluorescent proteins that exhibit properties not currently available in the limited number of known fluorescent proteins as well as DNAs encoding them that do not suffer from the drawbacks of the known GFP.

SUMMARY OF THE INVENTION

The present invention provides nucleic acid molecules encoding novel fluorescent proteins and mutants, and derivatives thereof. Said nucleic acid may be isolated, synthesized or present in its non-natural environment.

In certain embodiments, the nucleic acid of the present invention is isolated from copepods (phylum Arthropoda, subphylum Crustacea; class Maxillopoda; subclass Copepoda) or mutants or derivatives thereof.

In certain embodiments, the nucleic acid of the present invention encodes a protein that has an amino acid sequence, selected from the group consisting of SEQ ID NOs: 2, 4, 6, 8, 10, 12, 14, 16, 18, 20, 22, 24, 26, or 28. In certain embodiments, the nucleic acid encodes a homologue, mutant, derivative, mimetic or a fragment of said protein.

In certain embodiments, the nucleic acid of the present invention has a nucleotide sequence selected from the group consisting of SEQ ID NOs: 1, 3, 5, 7, 9, 11, 13, 15, 17, 19, 21, 23, 25, or 27 or that is homologous, substantially the same, or identical thereto. Nucleic acid sequences that differ from the nucleic acid sequences of the present due to the degeneracy of genetic code or hybridize thereto, are also within the scope of the present invention.

In another embodiments, the invention is directed to proteins that are encoded by the subject nucleic acids, or substantially similar thereto, or homologues, derivatives, or mutants thereof, or is directed to fusion proteins comprising the proteins of the present invention.

Fragments of the nucleic acids of the present invention and nucleic acids that hybridize under stringent conditions to the nucleic acids of the present invention are also provided.

In yet other embodiments there are provided vectors comprising a nucleic acid of the present invention. In addition, the present invention provides expression cassettes comprising a nucleic acid of the present invention and regulatory elements necessary for expression of the nucleic acid in the desired host-cell.

In yet another embodiment, there are provided methods of producing a fluorescent protein of the present invention comprising expressing of a protein in a suitable host-cell and isolating the protein therefrom. Said method comprises (a) providing a nucleic acid molecule of present invention encoding fluorescent protein operably linked to suitable expression regulatory elements, (b) expressing the flourescent protein from said nucleic acid molecule, and (c) isolating the protein substantially free from other proteins.

In addition, antibodies specifically binding to the proteins of the present invention or fragments thereof are provided.

Additionally, host-cells, stable cell lines, transgenic animals and transgenic plants comprising nucleic acids, vectors or expression cassettes of the present invention are provided.

In yet another embodiment, oligonucleotides or probes comprising the nucleotide sequences capable of hybridizing to the subject nucleic acids are provided.

Also provided are methods that use a fluorescent protein of the present invention or the nucleic acid encoding it.

In preferred embodiment the method for labeling a biological molecule is provided, said method comprising coupling said biological molecule to the protein of the present invention.

In another preferred embodiment the method for labeling a cell is provided, said method comprising production of the protein of the present invention in the cell.

In another preferred embodiment the method for labeling a cell organelle is provided, said method comprising production of the protein of the present invention fused to a suitable subcellular localization signal in the cell.

In yet another preferred embodiment the method for analyzing a biological molecule, cell or cell organelle is provided, said method comprising detection of a fluorescence signal from protein of the present invention.

In yet another preferred embodiment the method for analyzing a biological molecule, cell or cell organelle is provided, said method comprising expression of a nucleic acid molecule of the present invention in a cell.

Additionally, kits comprising nucleic acids or vectors or expression cassettes harboring said nucleic acids, or proteins of the present invention are provided.

BRIEF DESCRIPTION OF THE FIGURES

FIG. 1 shows sequence alignment of novel copepod fluorescent proteins with *A. victoria* GFP and DsRed. Numbering is based on GFP. Introduced gaps are shown by dots. Copepod GFPs are compared with ppluGFP1: in their sequences residues identical to the corresponding amino acids in ppluGFP1 are represented by dashes.

DETAILED DESCRIPTION OF THE INVENTION

Figure 2:
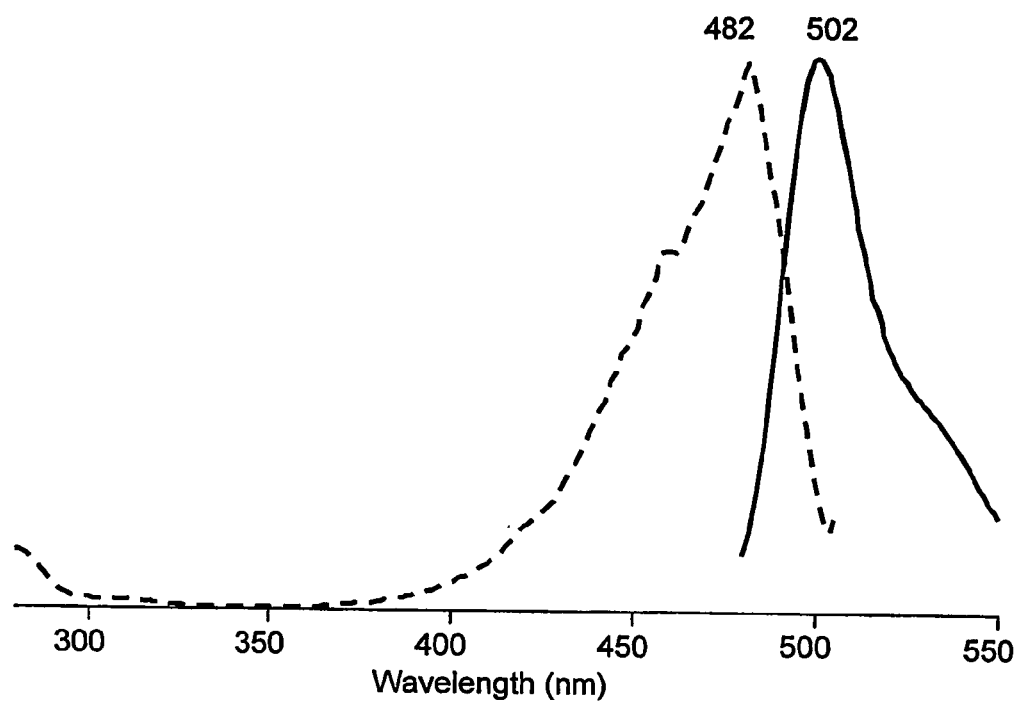
FIG. 2 illustrates the excitation (dashed line) and emission (solid line) spectra for wild type ppluGFP1 (ppluGFP2 possesses essentially the same spectra).
Figure 3:
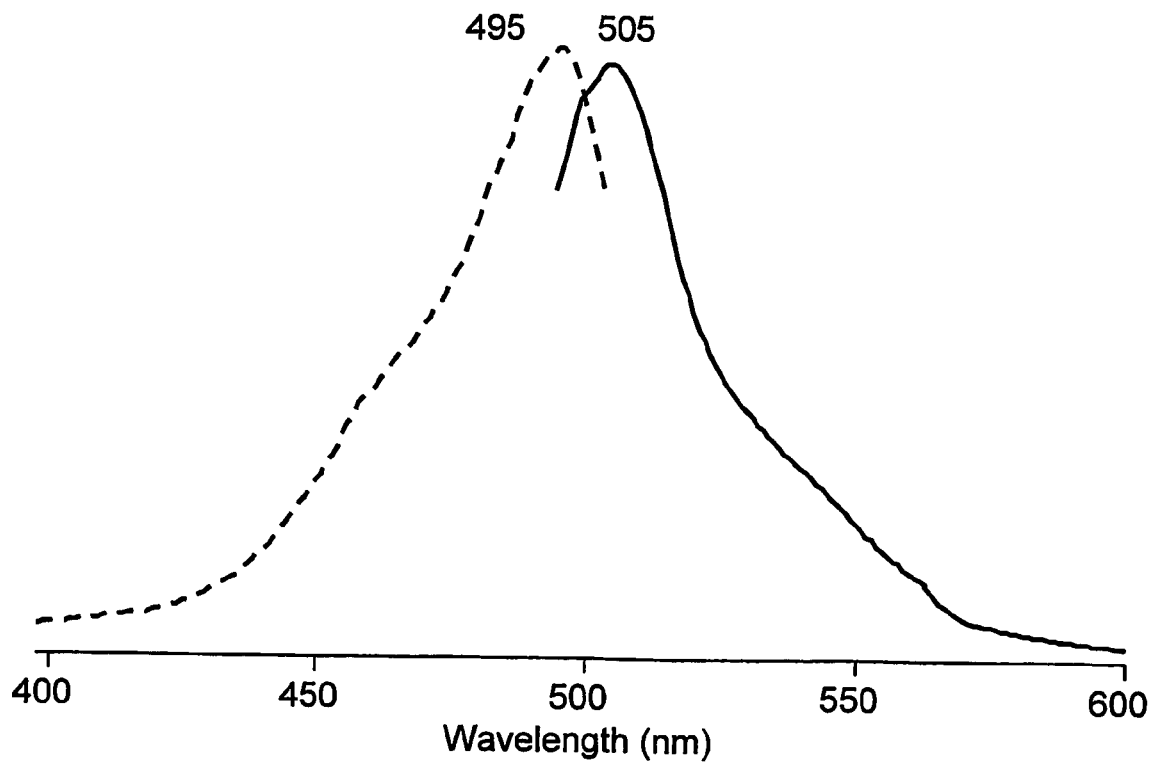
FIG. 3 illustrates the excitation (dashed line) and emission (solid line) spectra for wild type laesGFP.
Figure 4:
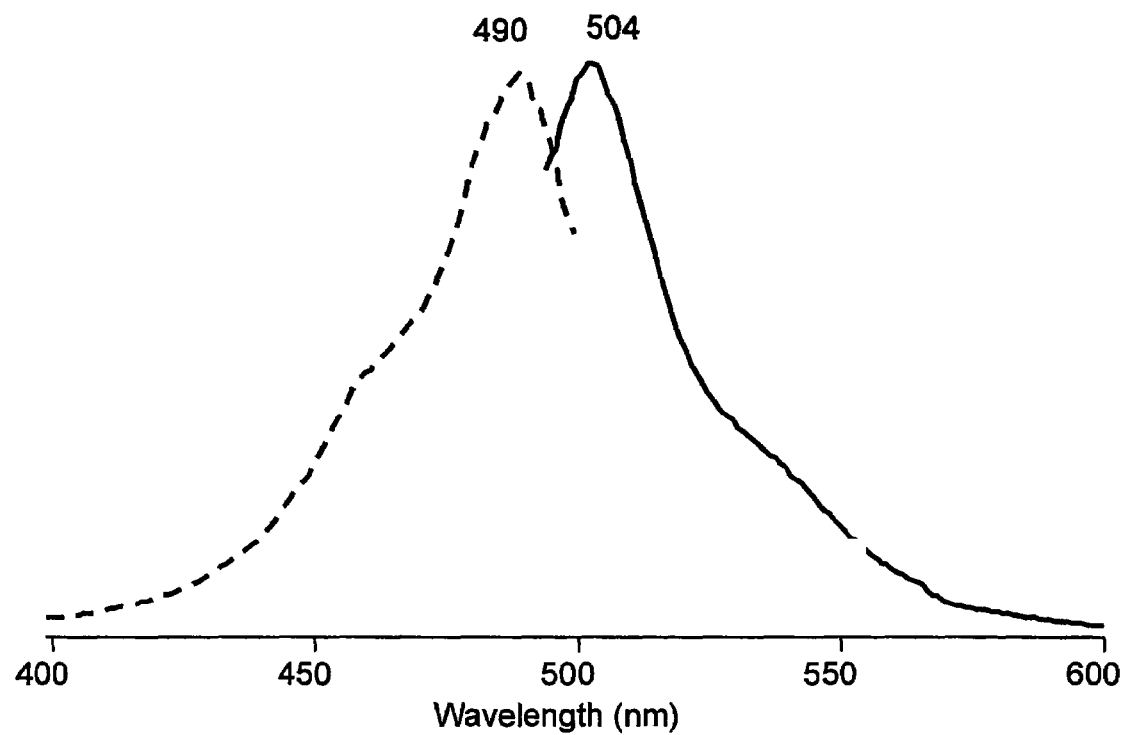
FIG. 4 illustrates the excitation (dashed line) and emission (solid line) spectra for wild type pmeaGFP1.
Figure 5:
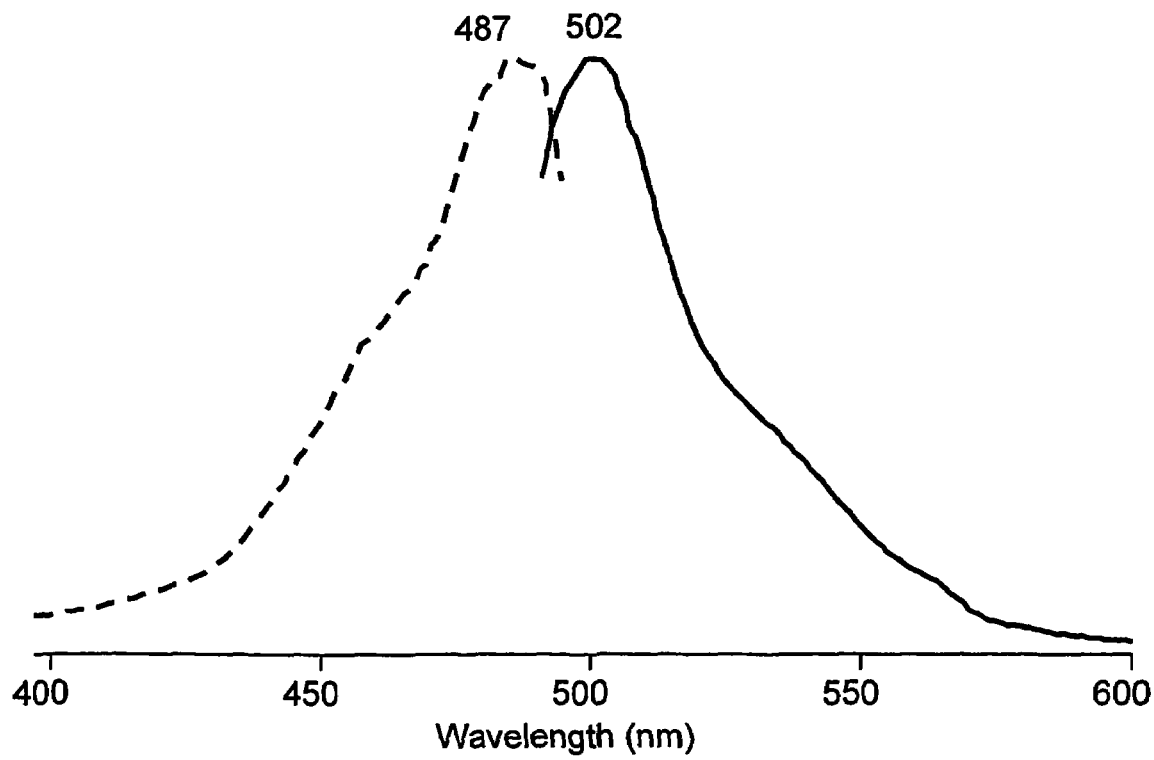
FIG. 5 illustrates the excitation (dashed line) and emission (solid line) spectra for wild type pmeaGFP2.
Figure 6:
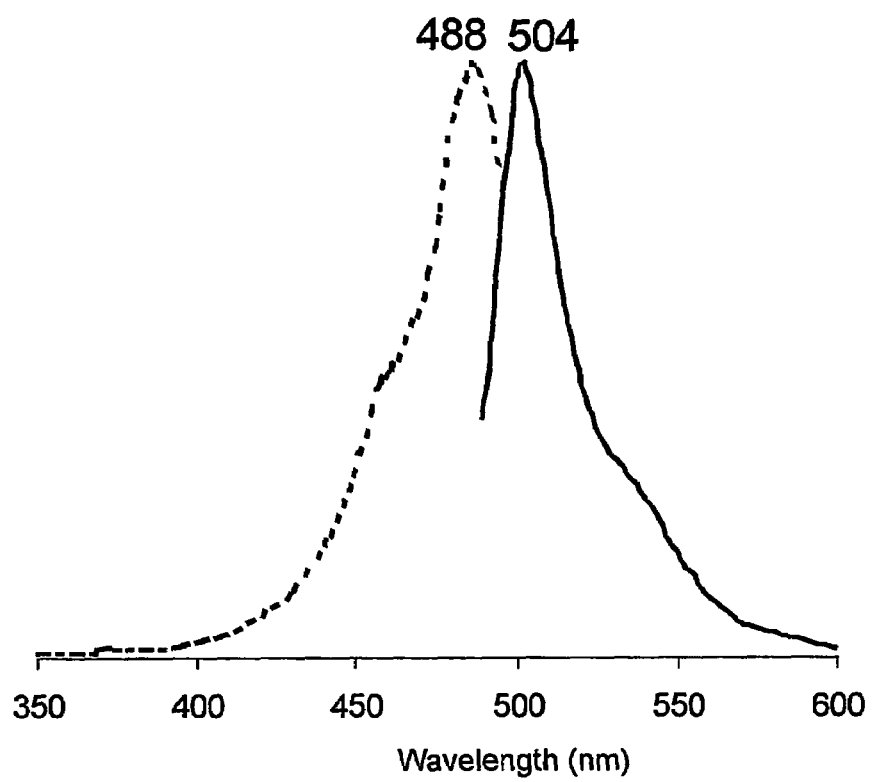
FIG. 6 illustrates the excitation (dashed line) and emission (solid line) spectra for wild type pmedGFP1.
Figure 7:
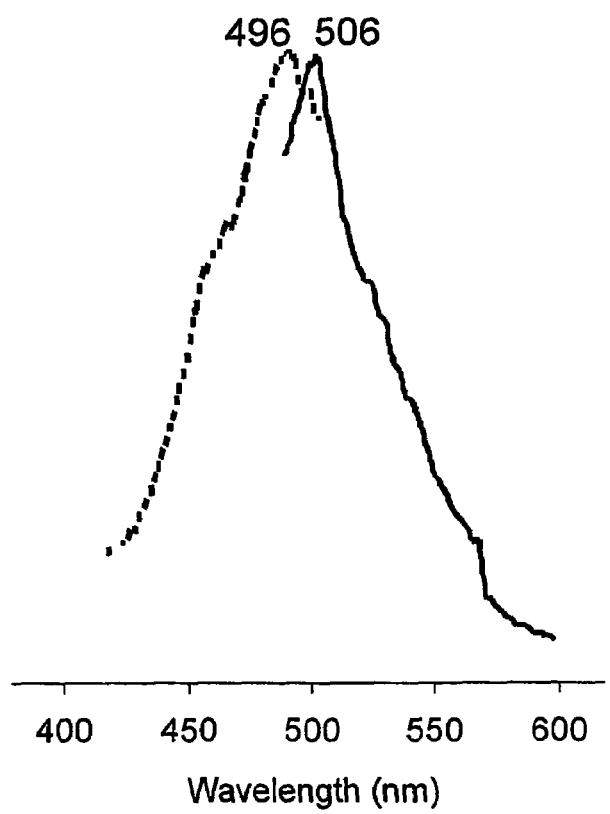
FIG. 7 illustrates the excitation (dashed line) and emission (solid line) spectra for wild type pmedGFP2.
Figure 8:
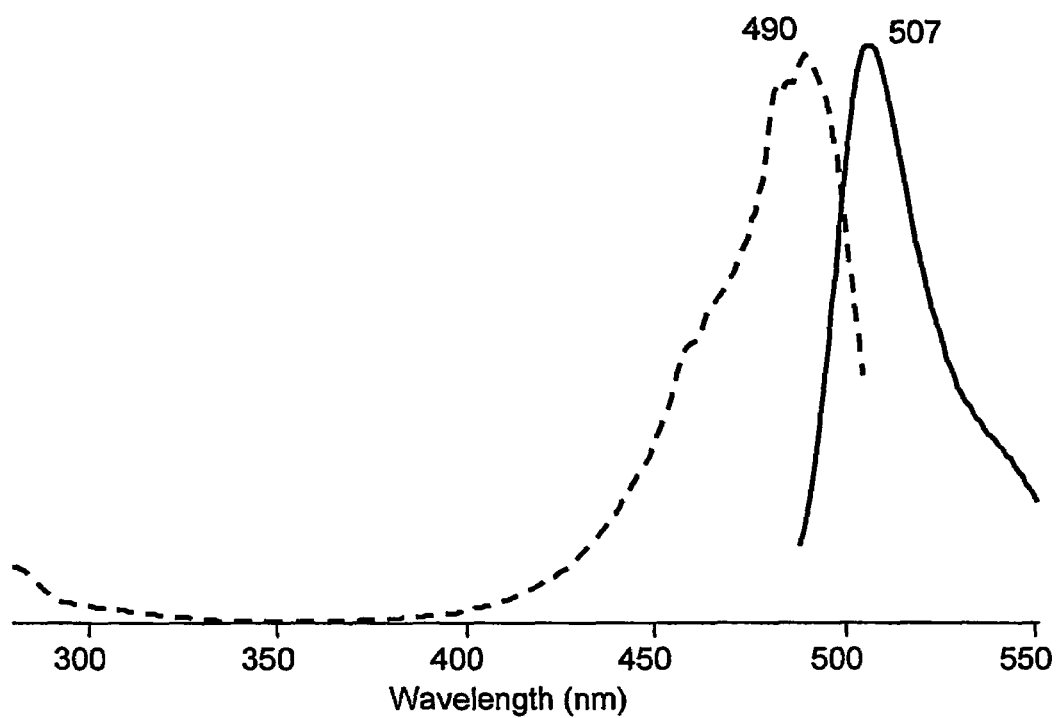
FIG. 8 illustrates the excitation (dashed line) and emission (solid line) spectra for wild type pdaelGFP.

As summarized above the present invention is directed to nucleic acid molecules encoding a fluorescent proteins and mutants, variants and derivatives thereof, as well as proteins and peptides encoded by these nucleic acids. The nucleic acid molecules and proteins of interest are isolated from copepod species. The proteins of interest include green fluorescent proteins, ppluGFP1 (SEQ ID NO: 2), ppluGFP2 (i.e. CopGFP, SEQ ID NO: 4), laesGFP (SEQ ID NO: 6), pmeaGFP1 (SEQ ID NO: 8), pmeaGFP2 (SEQ ID NO: 10), pdaelGFP (SEQ ID NO: 16), pmedGFP1 (SEQ ID NO: 12) and pmedGFP2 (SEQ ID NO: 14). Also of interest are proteins that are substantially similar to, or derivatives, or homologues, or mutants of, the above-referenced specific proteins. Also provided are fragments of the nucleic acids and the peptides encoded thereby, as well as antibodies specific to the proteins and peptides of the invention. In addition, host-cells, stable cell lines and transgenic organisms comprising above-referenced nucleic acid molecules are provided. The subject protein and nucleic acid compositions find use in a variety of different applications and methods, particularly protein labeling applications. Finally, kits for use in such methods and applications are provided.

Nucleic Acid Molecules

The present invention provides nucleic acid molecules encoding fluorescent proteins from copepods, derivatives, mutants, and homologues of these proteins, as well as fragments thereof. A nucleic acid molecule as used herein is DNA molecules, such as genomic DNA molecules or cDNA molecules, or RNA molecules, such as mRNA molecules. In particular, said nucleic acid molecules is cDNA molecules having an open reading frame that encodes a copepod fluorescent protein of the invention or fragment thereof and is capable, under appropriate conditions, of being expressed as a fluorescent protein or protein fragment (peptide) according to the invention. The invention also encompasses nucleic acids that are homologous, substantially similar to, identical to, derived from, or mimetics of the nucleic acids encoding proteins or protein fragments of the present invention. The subject nucleic acids are present in an environment other than their natural environment; e.g., they are isolated, present in enriched amounts, or are present or expressed in vitro or in a cell or organism other than their naturally occurring environment.

Specific nucleic acid molecules of interest may be isolated from an organism from phylum Arthropoda, preferably from subphylum Crustacea, more preferably from class Maxillopoda, more preferably from subclass Copepoda, more preferably from order Calanoida and even more preferably from family Pontellidae.

Specific nucleic acid molecules of interest include nucleic acid molecules that encode following copepod green fluorescent proteins (and homologs/derivates/mutants thereof): ppluGFP1, ppluGFP2 proteins from *Pontellina plumata*, laesGFP from *Labidocera aestiva*, pmeaGFP1 and pmeaGFP2 from cf. *Pontella meadi* Wheeler, pmedGFP1 and pmedGFP2 from *Pontella mediterranea* and pdaelGFP from an unidentified *Pontellidae* species. Each of these particular types of nucleic acid molecules of interest is discussed below in more details in the experimental part. Homologues/mutants/derivates of these proteins such as CopCFP, CopGFP-NA1-3 described below in more details in the experimental part are also of particular interest. The deduced wild type cDNA coding sequences for these proteins are depicted in SEQ ID NOs: 1, 3, 5, 7, 9, 11, 13, 15.

Homologs of the above-described nucleic acid molecules are also of interest. The source of homologous nucleic acids may be any species of plant or animal or the sequence may be wholly or partially synthetic including nucleic acid mimetics. In certain embodiments, the nucleic acid of the present invention has a sequence identity to corresponding homologs on the nucleotide or amino acid levels of at least about 40%, and, preferably about 50%, 55%, 60%, 65%, 70%, or higher, including 75%, 80%, 85%, 90% and 95% or higher. A reference sequence will usually be at least about 30 nucleotides long, more usually at least about 60 nucleotides long, and may extend to the complete sequence that is being compared. Sequence similarity is calculated based on a reference sequence. Algorithms for sequence analysis are known in the art, such as BLAST, described in Altschul et al., J. Mol. Biol., 215, pp. 403-10 (1990) (for example, using default settings, i.e., parameters w=4 and T=17).

Homologs are identified by any of a number of methods. A fragment of a cDNA of the present invention may be used as a hybridization probe against a cDNA library from a target organism using low stringency conditions. The probe may be a large fragment, or one or more short degenerate primers. Nucleic acids having sequence similarity are detected by hybridization under low stringency conditions, for example, at 50° C. and 6×SSC (0.9 M sodium chloride/0.9 M sodium citrate) followed by washing at 55° C. in 1×SSC (150 mM sodium chloride/15 mM sodium citrate). Sequence identity may be determined by hybridization under high stringency conditions, for example, at 50° C. or higher and 0.1×SSC (15 mM sodium chloride/1.5 mM sodium citrate). Nucleic acids having a region of substantial identity to the provided sequences, e.g., allelic variants, genetically-altered versions of the nucleic acid, etc., bind to the provided sequences under high stringency hybridization conditions. By using probes, particularly labeled probes of DNA sequences, one can isolate homologous or related genes.

Also provided are nucleic acids that hybridize to the above-described nucleic acids under stringent conditions, preferably under high stringency conditions (i.e., complements of the previously-described nucleic acids). An example of stringent conditions is hybridization at 50° C. or higher and 0.1×SSC (15 mM sodium chloride/1.5 mM sodium citrate). Another example of high stringency hybridization conditions is overnight incubation at 42° C. in a solution of 50% formamide, 5×SSC, 50 mM sodium phosphate (pH7.6), 5×Denhardt's solution, 10% destran sulfate, and 20 µg/ml denatured, sheared salmon sperm DNA, followed by washing in 0.1× SSC at about 65° C. Other high stringency hybridization conditions are known in the art and may also be used to identify nucleic acids of the invention.

Nucleic acids encoding variants, mutants or derivatives of the proteins of the invention also are provided. Mutants or derivates can be generated on a template nucleic acid selected from the described-above nucleic acids by modifying, deleting or adding one or more nucleotides in the template sequence, or a combination thereof, to generate a variant of the template nucleic acid. The modifications, additions or deletions can be introduced by any method known in the art (see for example Gustin et al., Biotechniques (1993) 14: 22; Barany, Gene (1985) 37: 111-123; and Colicelli et al., Mol. Gen. Genet. (1985) 199:537-539, Sambrook et al., Molecular Cloning: A Laboratory Manual, (1989), CSH Press, pp. 15.3-15.108) including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-directed mutagenesis, random mutagenesis, gene reassembly, gene site saturated mutagenesis (GSSM), synthetic ligation reassembly (SLR), or a combination thereof. The modifications, additions or deletions may be also introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof. In some embodiments, fluorescent proteins encoded by mutant or derived nucleic acids have the same fluorescent or biochemical properties as the wild type fluorescent protein. In other embodiments, mutant or derived nucleic acids encode fluorescent proteins with altered properties, as described in more detail for mutants CopCFP, CopGFP-NA1-3, infra.

In addition, degenerated variants of the nucleic acids that encode the proteins of the present invention are also provided. Degenerated variants of nucleic acids comprise replacements of the codons of the nucleic acid with other codons encoding the same amino acids. In particular, degenerated variants of the nucleic acids are generated to increase its expression in a host cell. In this embodiment, codons of the nucleic acid that are non-preferred or a less preferred in genes in the host cell are replaced with the codons over-represented in coding sequences in genes in the host cell, wherein said replaced codons encodes the same amino acid. Humanized versions of the nucleic acids of the present invention are under particular interest. As used herein, the term "humanized" refers to changes made to the nucleic acid sequence to optimize the codons for expression of the protein in mammalian (human) cells (Yang et al., Nucleic Acids Research (1996) 24: 4592-4593). See also U.S. Pat. No. 5,795,737 which describes humanization of proteins, the disclosure of which is herein incorporated by reference. Examples of degenerated variants of interest are described in more details in experimental part, infra.

The term "cDNA" as used herein is intended to include nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest may comprise the nucleic acid present between the initiation codon and the stop codon, as defined in the listed sequences, including all of the introns that are normally present in a native chromosome. The genomic sequence of interest may further include 5' an 3' non-translated regions found in the mature mRNA, as well as specific transcriptional and translational regulatory sequences, such as promoters, enhancers, etc., including about 1 kb, but possibly more, of flanking genomic DNA at either the 5' or 3' end of the transcribed region.

The nucleic acid molecules of the invention may encode all or a part of the subject proteins. Double- or single-stranded fragments may be obtained from the DNA sequence by chemically synthesizing oligonucleotides in accordance with conventional methods, by restriction enzyme digestion, by PCR amplification, etc. For the most part, DNA fragments will be at least about 15 nucleotides in length, usually at least about 18 nucleotides in length or about 25 nucleotides in length, and may be at least about 50 nucleotides in length. In some embodiments, the subject nucleotide acid molecules may be about 100, about 200, about 300, about 400, about 500, about 600, about 700 nucleotides or greater in length. The subject nucleic acids may encode fragments of the subject proteins or the full-length proteins; e.g., the subject nucleic acids may encode polypeptides of about 25 amino acids, about 50, about 75, about 100, about 125, about 150, about 200 amino acids up to the full length protein.

The subject nucleic acids may be isolated and obtained in substantially purified form. Substantially purified form means that the nucleic acids are at least about 50% pure, usually at least about 90% pure and are typically "recombinant", i.e., flanked by one or more nucleotides with which it is not normally associated on a naturally-occurring chromosome in its natural host organism.

The nucleic acids of the present invention, e.g. having the sequence of SEQ ID NOs: 1, 3, 5, 7, 9, 11, 13, 15, 17, 19, 21, 23, 25, or 27, the corresponding cDNAs, full-length genes and constructs can be generated synthetically by a number of different protocols known to those of skill in the art. Appropriate nucleic acid constructs are purified using standard recombinant DNA techniques as described in, for example, Sambrook et al., Molecular Cloning: A Laboratory Manual, $2^{nd}$ Ed., (1989) Cold Spring Harbor Press, Cold Spring Harbor, N.Y., and under regulations described in, e.g., United States Dept. of HHS, National Institute of Health (NIH) Guidelines for Recombinant DNA Research.

Also provided are nucleic acids that encode fusion proteins comprising a protein of the present invention, or fragments thereof that are discussed in more details below.

Also provided are vector and other nucleic acid constructs comprising the subject nucleic acids. Suitable vectors include viral and non-viral vectors, plasmids, cosmids, phages, etc., preferably plasmids, and used for cloning, amplifying, expressing, transferring etc. of the nucleic acid sequence of the present invention in the appropriate host. The choice of appropriate vector is well within the skill of the art, and many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems used inter alia for the production of the subject chromogenic or fluorescent proteins or fusion proteins thereof or for replication of the subject nucleic acid molecules. The expression cassette may exist as an extrachromosomal element or may be integrated into the genome of the cell as a result of introduction of said expression cassette into the cell. For expression, the gene product encoded by the nucleic acid of the invention is expressed in any convenient expression system, including, for example, bacterial, yeast, insect, amphibian, or mammalian systems. In the expression vector, a subject nucleic acid is operably linked to a regulatory sequence that can include promoters, enhancers, terminators, operators, repressors and inducers. Methods for preparing expression cassettes or systems capable of expressing the desired product are known for a person skilled in the art.

Cell lines, which stably express the proteins of present invention, can be selected by the methods known in the art (e.g. the co-transfection with a selectable marker such as dhfr, gpt, neomycin, hygromycin allows the identification and isolation of the transfected cells that contain the gene integrated into a genome).

The above-described expression systems may be used in prokaryotic or eukaryotic hosts. Host-cells such as *E. coli, B. subtilis, S. cerevisiae*, insect cells in combination with baculovirus vectors, or cells of a higher organism such as vertebrates, e.g., COS 7 cells, HEK 293, CHO, Xenopus oocytes, etc., may be used for production of the protein.

When any of the above-referenced host cells, or other appropriate host cells or organisms are used to replicate and/or express the nucleic acids of the invention, the resulting replicated nucleic acid, expressed protein or polypeptide is within the scope of the invention as a product of the host cell or organism. The product may be recovered by an appropriate means known in the art.

Also of interest are promoter sequences of the genomic sequences of the present invention, where the sequence of the 5' flanking region may be utilized for promoter elements, including enhancer binding sites, that, for example, provide for regulation of expression in cells/tissues where the subject proteins gene are expressed.

Also provided are small DNA fragments of the subject nucleic acids, that are useful as primers for PCR, hybridization screening probes, etc. Larger DNA fragments are useful for production of the encoded polypeptide, as described previously. However, for use in geometric amplification reactions, such as geometric PCR, a pair of small DNA fragments, i.e., primers, will be used. The exact composition of the primer sequences is not critical for the invention, but for most applications, the primers will hybridize to the subject sequence under stringent conditions, as is known in the art. It is preferable to choose a pair of primers that will generate an amplification product of at least about 50 nucleotides, preferably at least about 100 nucleotides and may extend to the complete sequence of the nucleic acid. Algorithms for the selection of primer sequences are generally known, and are available in commercial software packages. Amplification primers hybridize to complementary strands of DNA and will prime toward each other.

The nucleic acid molecules of the present invention also may be used to identify expression of a gene in a biological specimen. The manner in which one probes cells for the presence of particular nucleotide sequences, such as genomic DNA or RNA, is well established in the art. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g., nitrocellulose, nylon, etc., and then probed with a fragment of the subject DNA as a probe. Other techniques, such as oligonucleotide ligation assays, in situ hybridizations, and hybridization to DNA probes arrayed on a solid chip may also be used. Detection of mRNA hybridizing to the subject sequence is indicative of gene expression in the sample.

The subject nucleic acids, including flanking promoter regions and coding regions, may be mutated in various ways known in the art to generate targeted changes in promoter strength or to vary the sequence of the encoded protein or properties of the encoded protein, including the fluorescent properties of the encoded protein.

Proteins

Also provided by the subject invention are copepod fluorescent proteins, derivates, and mutants thereof including full-length proteins, as well as portions or fragments thereof. Also provided variants of the naturally occurring protein, where such variants are homologous or substantially similar to the naturally occurring protein, and mutants of the naturally occurring proteins, as described in greater detail below.

In many embodiments, the subject proteins have an absorbance maximum ranging from about 300 nm to 700 nm, usually from about 350 nm to 550 nm and more usually from about 450 to 550 nm, and often from about 470 to 520 nm, e.g., 470 to 500 nm while the emission spectra of the subject proteins typically ranges from about 400 nm to 700 nm, usually from about 450 nm to 650 nm and more usually from about 480 to 600 nm while in many embodiments the emission spectra ranges from about 480 to 550 nm, e.g., 490 to 520 nm, or 490 to 510 nm. The subject proteins generally have a maximum extinction coefficient that ranges from about 25,000 to 150,000 and usually from about 45,000 to 120,000, e.g., 50,000 to 100,000. The subject proteins typically range in length from about 150 to 300 amino acids and usually from about 200 to 300 amino acid residues, and generally have a molecular weight ranging from about 15 to 35 kDa, usually from about 17.5 to 32.5 kDa In certain embodiments, the subject proteins are bright, where by bright is meant that the chromo- and fluorescent proteins can be detected by common methods (e. g., visual screening, spectrophotometry, spectrofluorometry, fluorescent microscopy, by FACS machines, etc.) Fluorescence brightness of particular fluorescent proteins is determined by its quantum yield multiplied by maximal extinction coefficient. Brightness of a chromoproteins may be expressed by its maximal extinction coefficient.

In certain embodiments, the subject proteins fold rapidly following expression in the host cell. By rapidly folding is meant that the proteins achieve their tertiary structure that gives rise to their chromo- or fluorescent quality in a short period of time. In these embodiments, the proteins fold in a period of time that generally does not exceed about 3 days, usually does not exceed about 2 days and more usually does not exceed about 1 day.

Specific proteins of interest are fluoroproteins (and homologs, mutants, and derivates thereof) from the phylum Arthropoda, preferably from subphylum Crustacea, more preferably from class Maxillopoda, more preferably from subclass Copepoda, more preferably from order Calanoida and even more preferably from family Pontellidae.

Specific proteins of interest include following copepod green fluorescent proteins (and homologs/derivates/mutants thereof): ppluGFP1, ppluGFP2 proteins from *Pontellina plumata*, laesGFP from *Labidocera aestiva*, pmeaGFP1 and pmeaGFP2 from cf. *Pontella meadi* Wheeler, pmedGFP1 and pmedGFP2 from *Pontella mediterranea* and pdaelGFP from an unidentified *Pontellidae* species. Each of these particular types of proteins of interest is discussed in more details in the experimental part, infra. The wild type amino acid sequences for these proteins are depicted in SEQ ID NOs: 2, 4, 6, 8, 10, 12, 14, 16. Homologues/mutants/derivates of these proteins such as CopCFP, CopGFP-NA1, CopGFP-NA2, CopGFP-NA3 described below in more details in the experimental part are also of particular interest.

Homologs or proteins that vary in sequence from the above provided specific amino acid sequences of the subject invention, i. e., SEQ ID NOs: 2, 4, 6, 8, 10, 12, 14, 16, 18, 20, 22, 24, 26, or 28, are also provided. By homolog is meant a protein having at least about a protein having at least about 50%, usually at least about 55% and more usually at least about 60% amino acid sequence identity to amino acid sequences of SEQ ID NOs: 2, 4, 6, 8, 10, 12, 14, 16, 18, 20, 22, 24, 26, or 28 as determined using MegAlign, DNAstar clustal algorithm as described in D. G. Higgins and P. M. Sharp, "Fast and Sensitive multiple Sequence Alignments on a Microcomputer," CABIOS, 5 pp. 151-3 (1989) (using parameters ktuple 1, gap penalty 3, window 5 and diagonals saved 5). In many embodiments, homologs of interest have much higher sequence identity e.g., 70%, 75%, 80%, 85%, 90% (e.g., 92%, 93%, 94%) or higher, e.g., 95%, 96%, 97%, 98%, 99%, 99.5%, particularly for the amino acid sequence that provides the functional regions of the protein.

Also provided are proteins that are substantially identical to the wild type protein, where by substantially identical is meant that the protein has an amino acid sequence identity to the sequence of wild type protein of at least about 60%, usually at least about 65% and more usually at least about 70%, where in some instances the identity may be much higher, e. g., 75%, 80%, 85%, 90%, 95% or higher.

Proteins that are derivatives or mutants of the above-described naturally occurring proteins are also provided. Mutants and derivatives may retain biological properties of the wild type (e.g., naturally occurring) proteins, or may have biological properties which differ from the wild type proteins. The term "biological property" of the proteins of the present invention refers to, but is not limited to, spectral properties, such as absorbance maximum, emission maximum, maximum extinction coefficient, brightness (e.g., as compared to the wild type protein or another reference protein such as green fluorescent protein (GFP) from *A. Victoria*), and the like; biochemical properties, such as in vivo and/or in vitro stability (e.g., half-life); maturation speed, aggregation tendency and oligomerization tendency and other such properties. Mutations include single amino acid changes, deletions or insertions of one or more amino acids, N-terminal truncations or extensions, C-terminal truncations or extensions and the like.

Mutants and derivates can be generated using standard techniques of molecular biology as described in details in the section "Nucleic acid molecules" above. Several mutants are described herein. Given the guidance provided in the Examples, and using standard techniques, those skilled in the art can readily generate a wide variety of additional mutants and test whether a biological (e.g. biochemical, spectral, etc.) property has been altered. For example, fluorescence intensity can be measured using a spectrophotometer at various excitation wavelengths.

Derivatives can be also generated using standard techniques that includes RNA-editing, chemical modifications, posttranslational and posttranscriptional modifications and the like. For instance, derivatives can be generated by processes such as altered phosphorylation, or glycosylation, or acetylation, or lipidation, or by different types of maturation cleavage and the like.

Those proteins of the subject invention that are naturally-occurring proteins are present in a non-naturally occurring environment, e.g., are separated from their naturally-occurring environment. For example, purified protein is provided, where "purified" means that the protein is present in a mixture that is substantially free of non-chromogenic or fluorescent proteins of interest, where "substantially free" means that less than 90%, usually less than 60% and more usually less than 50% of the mixture content is non-chromogenic or fluorescent proteins or mutants thereof. The proteins of the present invention also may be present in the isolated form, by which is meant that the protein is substantially free of other proteins and other naturally-occurring biological molecules, such as oligosaccharides, nucleic acids and fragments thereof, and the like, where the term "substantially free" in this instance means that less than 70%, usually less than 60% and more usually less than 50% of the composition containing the isolated protein is some other natural occurring biological molecule. In certain embodiments, the proteins are present in substantially purified form, where by "substantially purified form" means at least 95%, usually at least 97% and more usually at least 99% pure.

Fragments of the naturally-occurring proteins as well as of the mutant and derivate proteins described above are also provided. Biologically active fragments and/or fragments corresponding to functional domains, and the like are in a particular interest. Fragments of interest are polypeptides that are typically at least about 30 amino acids in length, usually at least about 50 amino acids in length, preferably of at least about 75 or 100 amino acids in length and may be as long as 300 amino acids in length or longer, but will usually not exceed about 250 amino acids in length, where the fragment will have a stretch of amino acids that is identical to the subject protein of at least about 25 amino acids, and usually at least about 45 amino acids, and in many embodiments at least about 50 amino acids in length. In some embodiments, the subject polypeptides are about 25 amino acids, about 50, about 75, about 100, about 125, about 150, about 200, or about 250 amino acids in length, up to the entire length of the protein. In some embodiments, a protein fragment retains all or substantially all of the specific property of the wild type protein.

The subject proteins and polypeptides may be obtained from naturally occurring sources or synthetically produced. For example, wild type proteins may be derived from biological sources which express the proteins, e.g., copepod species, such as the specific ones listed above. The subject proteins may also be derived from synthetic means, e.g. by expressing a recombinant nucleic acid coding sequence encoding the protein of interest in a suitable host, as described above. Any convenient protein purification procedures may be employed, where suitable protein purification methodologies are described in Guide to Protein Purification, (Deuthser ed., Academic Press, 1990). For example, a lysate may be prepared from the original source and purified using HPLC, exclusion chromatography, gel electrophoresis, affinity chromatography, and the like.

Also provided fusion proteins comprising a protein of the present invention, or fragments thereof, fused, for example, to a degradation sequence, a sequence of subcellular localization (e.g. nuclear localization signal, peroximal targeting signal, Golgi apparatus targeting sequence, mitochondrial targeting sequence, etc.), a signal peptide, or any protein or polypeptide of interest. Fusion proteins may comprise for example, a fluorescent protein of subject invention polypeptide and a second polypeptide ("the fusion partner") fused in-frame at the N-terminus and/or C-terminus of the fluorescent protein. Fusion partners include, but are not limited to, polypeptides that can bind antibodies specific to the fusion partner (e.g., epitope tags), antibodies or binding fragments thereof, polypeptides that provide a catalytic function or induce a cellular response, ligands or receptors or mimetics thereof, and the like. In such fusion proteins, the fusion partner is generally not naturally associated with the fluoro/chromo-protein portion of the fusion protein, and is typically not a copepod fluorescent proteins of subject invention or derivative/fragment thereof; i.e., it is not found in copepod species.

Also provided are antibodies that bind specifically to the fluorescent or chromo-proteins of the present invention. Suitable antibodies may be produced using the techniques known in the art. For example, polyclonal antibodies may be obtained as described in (Harlow and Lane Antibodies: A Laboratory Manual, (1988) Cold Spring Harbor Laboratory Press, Cold Spring Harbor, N.Y.) and monoclonal antibodies may be obtained as described in (Goding Monoclonal Antibodies: Principles and Practice: Production and Application of Monoclonal Antibodies in Cell Biology, Biochemistry and Immunology; 3rd edition, (1996) Academic Press). Chimeric antibodies including humanized antibodies as well as single-chain antibodies and antibody fragments such as Fv, F(ab')$_2$ and Fab are also of interest.

Transformants

The nucleic acids of the present invention can be used to generate transformants including transgenic organisms or site-specific gene modifications in cell lines. Transgenic cells of the subject invention include one or more nucleic acids according to the subject invention present as a transgene. For the purposes of the invention any suitable host cell may be used including prokaryotic (e.g. *Escherichia coli, Streptomyces* sp., *Bacillus subtilis, Lactobacillus acidophilus*, etc) or eukaryotic host-cells. Transgenic organism of the subject invention can be prokaryotic or a eukaryotic organism including bacteria, cyanobacteria, fungi, plants and animals, in which one or more of the cells of the organism contains heterologous nucleic acid of subject invention introduced by way of human intervention, such as by transgenic techniques well known in the art.

The isolated nucleic acid of the present invention can be introduced into the host by methods known in the art, for example infection, transfection, transformation or transconjugation. Techniques for transferring the nucleic acid molecules (i.e. DNA) into such organisms are widely known and provided in references such as Sambrook et al. (Molecular Cloning: A Laboratory Manual, $3^{nd}$-Ed., (2001) Cold Spring Harbor Press, Cold Spring Harbor, N.Y.).

In one embodiment, the transgenic organism can be a prokaryotic organism. Methods on the transformation of prokaryotic hosts are well documented in the art (for example see Sambrook et al. Molecular Cloning: A Laboratory Manual, 2nd edition (1989) Cold Spring Harbor Laboratory Press and Ausubel et al., Current Protocols in Molecular Biology (1995) John Wiley & Sons, Inc).

In another embodiment, the transgenic organism can be a fungus, for example yeast. Yeast is widely used as a vehicle for heterologous gene expression (for example see Goodey et al Yeast biotechnology, D R Berry et al, eds, (1987) Allen and Unwin, London, pp 401429) and by King et al Molecular and Cell Biology of Yeasts, E F Walton and G T Yarronton, eds, Blackie, Glasgow (1989) pp 107-133). Several types of yeast vectors are available, including integrative vectors, which require recombination with the host genome for their maintenance, and autonomously replicating plasmid vectors.

Another host organism is an animal. Transgenic animals can be obtained by transgenic techniques well known in the art and provided in references such as Pinkert, Transgenic Animal Technology: a Laboratory Handbook, 2nd edition (2203) San Diego: Academic Press; Gersenstein and Vintersten, Manipulating the Mouse Embryo: A Laboratory Manual, 3rd ed, (2002) Nagy A. (Ed), Cold Spring Harbor Laboratory; Blau et al., Laboratory Animal Medicine, 2nd Ed., (2002) Fox J. G., Anderson L. C., Loew F. M., Quimby F. W. (Eds), American Medical Association, American Psychological Association; Gene Targeting: A Practical Approach by Alexandra L. Joyner (Ed.) Oxford University Press; 2nd edition (2000). For example, transgenic animals can be obtained through homologous recombination, where the endogenous locus is altered. Alternatively, a nucleic acid construct is randomly integrated into the genome. Vectors for stable integration include plasmids, retroviruses and other animal viruses, YACs, and the like.

The nucleic acid can be introduced into the cell, directly or indirectly by introduction into a precursor of the cell, by way of deliberate genetic manipulation, such as by microinjection or by infection with a recombinant virus or with a recombinant viral vector and the like. The term genetic manipulation does not include classical cross-breeding, or in vitro fertilization, but rather is directed to the introduction of a recombinant nucleic acid molecule. This nucleic acid molecule may be integrated within a chromosome, or it may be extrachromosomally replicating DNA.

DNA constructs for homologous recombination will comprise at least a portion of a nucleic acid of the present invention, wherein the gene has the desired genetic modification(s), and includes regions of homology to the target locus. DNA constructs for random integration need not include regions of homology to mediate recombination. Conveniently, markers for positive and negative selection may be included. Methods for generating cells having targeted gene modifications through homologous recombination are known in the art. For various techniques for transfecting mammalian cells, see Keown et al., Meth. Enzymol. (1990) 185:527-537.

For embryonic stem (ES) cells, an ES cell line may be employed, or embryonic cells may be obtained freshly from a host, such as a mouse, rat, guinea pig, etc. Such cells are grown on an appropriate fibroblast-feeder layer or grown in the presence of leukemia inhibiting factor (LIF). Tansformed ES or embryonic cells may be used to produce transgenic animals using the appropriate technique described in the art.

The transgenic animals may be any non-human animals including non-human mammal (e.g. mouse, rat), a bird or an amphibian, etc., and used in functional studies, drug screening and the like. Representative examples of the use of transgenic animals include those described infra.

Transgenic plants also may be produced. Methods of preparing transgenic plant cells and plants are described in U.S. Pat. Nos. 5,767,367; 5,750,870; 5,739,409; 5,689,049; 5,689, 045; 5,674,731; 5,656,466; 5,633,155; 5,629,470; 5,595,896; 5,576,198; 5,538,879; 5,484,956; the disclosures of which are herein incorporated by reference. Methods of producing transgenic plants also are reviewed in Plant Biochemistry and Molecular Biology (eds. Lea and Leegood, John Wiley & Sons) (1993) pp. 275-295 and in Plant Biotechnology and Transgenic Plants (eds. Oksman-Caldentey and Barz), (2002) 719 p.

For example, embryogenic explants comprising somatic cells may be used for preparation of the transgenic host. Following cell or tissue harvesting, exogenous DNA of interest is introduced into the plant cells, where a variety of different techniques is available for such introduction. With isolated protoplasts, the opportunity arises for introduction via DNA-mediated gene transfer protocols, including incubation of the protoplasts with naked DNA, such as plasmids comprising the exogenous coding sequence of interest in the presence of polyvalent cations (for example, PEG or PLO); or electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, such as auxins and cytokinins.

Other suitable methods for producing plants may be used such as "gene-gun" approach or Agrobacterium-mediated transformation available for those skilled in the art.

Methods of Use

The fluorescent proteins of the present invention (as well as other components of the subject invention described above) find use in a variety of different applications. For example, they may be used in the methods for labeling, analyzing or detecting a biological molecule, cell or cell organelle. Representative uses for each of these types of proteins will be described below, where the uses described herein are merely exemplary and are in no way meant to limit the use of the proteins of the present invention to those described.

In a preferred embodiment relating to the method for labeling a biological molecule, cell or cell organelle, the subject proteins find use as in vivo labels (or reporter molecules) in cell and molecular biology assays. The assays of interest include but not limited to assays for gene expression, protein localization and co-localization, protein-protein interactions, protein-nucleic acid interactions, nucleic acid-nucleic acid interactions, cell and cell organelle localization and interactions, etc. The fluorescent proteins of the present invention find use as a biomolecule labels, or cell organelle labels in living and fixed cells; as a markers in cell or organelle fusion, as a cell or organelle integrity markers, as a transfection markers (e.g. as labels for selection of transfected cells containing an expression vector encoding at least one fluorescent protein of the invention), as real-time probe working at near physiological concentrations, etc.

Furthermore, the subject proteins may be used in the method for analyzing a biological molecule. For example, they find use for identifying and/or measuring the expression of protein or polypeptide of interest in biological material. This method comprises: i) introducing into a cell a nucleic acid molecule comprising a nucleotide sequence encoding a fluorescent protein according to the present invention wherein said nucleic acid molecule is operably linked to and under the control of an expression control sequence which moderates expression of said protein or polypeptide of interest; ii) expression of the said nucleic acid under suitable condition; and iii) detecting the fluorescence emission of the fluorescent protein as a means of measuring the expression of the protein of interest.

In particular, the subject proteins find use for identifying and/or measuring the expression and/or localization of protein or polypeptide of interest in biological material. This method comprises: i) introducing into a cell a nucleic acid molecule comprising a nucleotide sequence encoding a fluorescent protein according to the present invention wherein said nucleic acid molecule is fused with sequence encoding protein or polypeptide of interest and operably linked to and under the control of an expression control sequence which moderates expression of said protein or polypeptide of interest; ii) culturing the cell under conditions suitable for the expression of the protein of interest; and iii) detecting the fluorescence emission of the fluorescent protein as a means of measuring the expression/localization of the protein of interest.

The applications of interest include the use of the subject proteins in fluorescence resonance energy transfer (FRET) methods. In these methods, the subject proteins serve as donor and/or acceptors in combination with a second fluorescent protein or dye, for example, a fluorescent protein as described in Matz et al., Nature Biotechnology 17:969-973 (1999); a red-shifted mutants of green fluorescent protein from *Aequorea victoria*, for example, as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference; other fluorescent dyes such as coumarin and its derivatives, 7-amino-4-methylcoumarin and aminocoumarin; bodipy dyes; cascade blue; or fluorescein and its derivatives, such as fluorescein isothiocyanate and Oregon green; rhodamine dyes such as Texas red, tetramethylrhodamine, eosins and erythrosins; cyanine dyes such as Cy3 and Cy5; macrocyclic chealates of lenthaninde ions, such as quantum dye; and chemilumescent dyes such as luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference.

Specific examples of where FRET assays employing the subject fluorescent proteins may be used include, but are not limited to, the detection of protein-protein interactions, such as in a mammalian two-hybrid system, transcription factor dimerization, membrane protein multimerization, multiprotein complex formation; as a biosensor for a number of different events, where a peptide or protein covalently links a FRET fluorescent combination including the subject fluorescent proteins and the linking peptide or protein is, for example, a protease-specific substrate for caspase-mediated cleavage, a peptide that undergoes conformational change upon receiving a signal which increases or decreases FRET, such as a PKA regulatory domain (cAMP-sensor), a phosphorylation site (for example, where there is a phosphorylation site in the peptide or the peptide has binding specificity to phosphorylated/dephosphorylated domain of another protein), or the peptide has $Ca^{2+}$ binding domain. In addition, fluorescence resonance energy transfer or FRET applications in which the proteins of the present invention find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; 5,439,797; the disclosures of which are herein incorporated by reference.

The fluorescent proteins of the present invention find use in a method for detecting the effects of a test substance on the regulation of expression and/or translocation of one or more proteins of interest in a cell. Alternatively, they find use in a method for detecting the expression of a protein of interest and the simultaneous activity of an expression control sequence in response to a test substance. The fluorescent proteins find also use in a method to compare the activity of two or more expression control sequences in a cell in response to a test substance. Such methods may be performed in the presence and in the absence of a test substance whose effect on the process is to be measured.

The fluorescent proteins of the present invention also find use in applications involving the automated screening of arrays of cells expressing fluorescent reporting groups by using microscopic imaging and electronic analysis. Screening can be used for drug discovery and in the field of functional genomics where the subject proteins are used as markers of whole cells to detect changes in multicellular reorganization and migration, for example in the formation of multicellular tubules (blood vessel formation) by endothelial cells, migration of cells through the Fluoroblok Insert system (Becton Dickinson Co.), wound healing, or neurite outgrowth. Screening can also be employed where the proteins of the present invention are used as markers fused to peptides (such as targeting sequences) or proteins that detect changes in intracellular location as an indicator for cellular activity, for example in signal transduction, such as kinase and transcription factor translocation upon stimuli. Examples include protein kinase C, protein kinase A, transcription factor NFkB, and NFAT; cell cycle proteins, such as cyclin A, cyclin B1 and cyclin E; protease cleavage with subsequent movement of cleaved substrate; phospholipids, with markers for intracellular structures such as the endoplasmic reticulum, Golgi apparatus, mitochondria, peroxisomes, nucleus, nucleoli, plasma membrane, histones, endosomes, lysosomes, or microtubules.

The proteins of the present invention also can be used in high content screening to detect co-localization of other fluorescent fusion proteins with localization markers as indicators of movements of intracellular fluorescent proteins/peptides or as markers alone. Examples of applications involving the automated screening of arrays of cells in which the subject fluorescent proteins find use include U.S. Pat. No. 5,989,835; as well as WO 0017624; WO 00/26408; WO 00/17643; and WO 00/03246; the disclosures of which are herein incorporated by reference.

The fluorescent proteins of the present invention also find use in high throughput screening assays. The subject fluorescent proteins are stable proteins with half-lives of more than 24 hours. Also provided are destabilized versions of the subject fluorescent proteins with decreased half-lives that can be used as transcription reporters for drug discovery. For example, a protein according to the subject invention can be fused with a putative proteolytic signal sequence derived from a protein with shorter half-life, such as a PEST sequence from the mouse ornithine decarboxylase gene, a mouse cyclin B1 destruction box or ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject fluorescent proteins for drug screening such as, for example, AP1, NFAT, NFkB, Smad, STAT, p53, E2F, Rb, myc, CRE, ER, GR and TRE, and the like.

The subject proteins can be used as second messenger detectors by fusing the subject proteins to specific domains such as the PKCgamma Ca binding domain, PKCgamma DAG binding domain, SH2 domain or SH3 domain, etc.

Secreted forms of the subject proteins, which in turn can be used in a variety of different applications can be prepared by fusing secreted leading sequences to the subject proteins.

The subject proteins also find use in fluorescence activated cell sorting (FACS) applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo labels in transgenic animals. For example, expression of the subject protein can be driven by tissue-specific promoters, where such methods find use in research for gene therapy, such as testing efficiency of transgenic expression, among other applications. A representative application of fluorescent proteins in transgenic animals that illustrates such applications is found in WO 00/02997, the disclosure of which is herein incorporated by reference.

Additional applications of the proteins of the present invention include use as markers following injection into cells or animals and in calibration for quantitative measurements; as markers or reporters in oxygen biosensor devices for monitoring cell viability; as markers or labels for animals, pets, toys, food, and the like.

The subject fluorescent proteins also find use in protease cleavage assays. For example, cleavage-inactivated fluorescence assays can be developed using the subject proteins, where the subject proteins are engineered to include a protease-specific cleavage sequence without destroying the fluorescent character of the protein. Upon cleavage of the fluorescent protein by an activated protease, fluorescence would sharply decrease due to the destruction of the functional chromophore. Alternatively, cleavage-activated fluorescence can be developed using the proteins of the present invention where the proteins are engineered to contain an additional spacer sequence in close proximity/or inside the chromophore. This variant is significantly decreased in its fluorescent activity, because parts of the functional chromophore are divided by the spacer. The spacer is framed by two identical protease-specific cleavage sites. Upon cleavage via the activated protease, the spacer would be cut out and the two residual "subunits" of the fluorescent protein would be able to reassemble to generate a functional fluorescent protein. Both of the above applications could be developed in assays for a variety of different types of proteases, such as caspases and others.

The subject proteins also can be used in assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes, while allowing co-localization of membrane proteins in specific phospholipid rafts, can be accomplished with the subject proteins.

The subject fluorescent proteins also find use as biosensors in prokaryotic and eukaryotic cells, such as a $Ca^{2+}$ ion indicator; a pH indicator, a phosphorylation indicator, or as an indicator of other ions, such as magnesium, sodium, potassium, chloride and halides. Methods of using fluorescent proteins as biosensors also include those described in U.S. Pat. Nos. 5,972,638; 5,824,485 and 5,650,135 (as well as the references cited therein) the disclosures of which are herein incorporated by reference.

The antibodies of the subject invention, described above, also find use in a number of applications, including the differentiation of the subject proteins from other fluorescent proteins.

Kits

Also provided by the present invention are kits for use in practicing one or more of the above-described applications. In preferred embodiments kits may be used for labeling a biological molecule. Kits typically include the protein of the invention as such, or a nucleic acid encoding the same preferably with the elements for expressing the subject proteins, for example, a construct such as a vector comprising a nucleic acid encoding the subject protein. The invention also encompasses means for producing such kit components. Said means may include the cDNA from copepods and pair of oligonucleotide primers to produce nucleic acid of subject invention, e.g. by PCR, or said means may include a number of the nucleic acid fragments, that when ligated can produce the nucleic acid encoding fluorescent protein of the present invention, etc. The kit components are typically present in a suitable storage medium, such as a buffered solution, typically in a suitable container. Also present in the kits may be antibodies specific to the provided protein. In certain embodiments, the kit comprises a plurality of different vectors each encoding the subject protein, where the vectors are designed for expression in different environments and/or under different conditions, for example, constitutive expression where the vector includes a strong promoter for expression in mammalian cells or a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit.

The following example is offered by way of illustration and not by way of limitation.

EXAMPLES

Example 1

Cloning of Fluorescent Protein cDNAs from Copepod Species

Several small (about 0.5-1 mm in length) Copepoda specimens (phylum Arthropoda; subphylum Crustacea; class Maxillopoda; subclass Copepoda; order Calanoida; family Pontellidae) that are possessed bright green fluorescence were selected from plankton samples.

To search for fluorescent proteins from these copepods a strategy based on screening of expression cDNA library in *E. coli* was used. Total RNA was isolated from the single organism by a NucleoSpin RNA II kit (Clontech). Amplified cDNA sample was prepared using a SMART cDNA amplification kit (Clontech) and cloned into the PCR-Script vector (Stratagene). About $5 \times 10^4$ recombinant clones were screened visually using a fluorescent stereomicroscope. As a result, several closely related (more than 63% identity, see, Table 1) novel GFP-like proteins were identified: ppluGFP1 (SEQ ID NOs: 1 and 2) and ppluGFP2 (SEQ ID NOs: 3 and 4) from *Pontellina plumata*; laesGFP (SEQ ID NOs: 5 and 6) from *Labidocera aestiva*; pmeaGFP1 (SEQ ID NOs: 7 and 8) and pmeaGFP2 (SEQ ID NOs: 9 and 10) from cf. *Pontella meadi* Wheeler; pmedGFP1 (SEQ ID NOs: 11 and 12) and pmedGFP2 (SEQ ID NOs: 13 and 14) from *Pontella mediterranea*; and pdaelGFP (SEQ ID NOs: 15 and 16) from an unidentified copepod species. Copepod GFPs shared approximately 25% and 18% amino acid identity with DsRed and *A. victoria* GFP, respectively (FIG. 1).

TABLE 1

Levels of amino acid identity between copepod GFPs.

|  | ppluGFP1 | ppluGFP2 | laesGFP | pmeaGFP1 | pmeaGFP2 | pdae1GFP | pmedGFP1 |
|---|---|---|---|---|---|---|---|
| ppluGFP1 |  |  |  |  |  |  |  |
| ppluGFP2 | 97% |  |  |  |  |  |  |
| laesGFP | 71% | 70% |  |  |  |  |  |
| pmeaGFP1 | 64% | 63% | 82% |  |  |  |  |
| pmeaGFP2 | 65% | 64% | 80% | 93% |  |  |  |
| pdae1GFP | 75% | 75% | 76% | 71% | 72% |  |  |
| pmedGFP1 | 68% | 67% | 86% | 84% | 83% | 76% |  |
| pmedGFP2 | 68% | 68% | 87% | 85% | 85% | 75% | 95% |

Example 2

Characterization of Copepod Fluorescent Proteins

The nucleic acid coding sequences of copepod fluorescent proteins were obtained as described above in the Example 1 and cloned into a pQE30 expressing vector (Qiagen), so that recombinant proteins contained a six-histidine tag at its N-terminus. After expression in *E. coli*, the proteins were purified via a metal-affinity resin TALON (Clontech) and characterized.

All proteins demonstrated green fluorescence and possessed similar but not identical excitation-emission spectral peaks at 482-495 and 502-507 nm, respectively (FIGS. 2-8). In contrast to the wild type *A. victoria* GFP, the novel proteins possessed only one absorption-excitation peak, which probably corresponds to deprotonated chromophore state.

ppluGFP2 was investigated in more detail. Purified ppluGFP2 possessed a molar extinction coefficient of 70,000 $M^{-1}cm^{-1}$ and a fluorescence quantum yield of 0.60. For the molar extinction coefficient determination, mature chromophore concentration was estimated. Protein was alkali-denatured with an equal volume of 2M NaOH. Under these conditions, the GFP-like chromophore absorbs at 446 nm and its molar extinction coefficient is 44,000 $M^{-1}cm^{-1}$ (Ward, W. W., Bioluminescence and Chemiluminescence (1981), Academic Press, 235-242). The absorption spectra for native and alkali-denatured ppluGFP2 were measured. The molar extinction coefficient for the native state protein was estimated based on the absorption of the denatured protein. For quantum yield determination, the fluorescence of ppluGFP2 was compared to equally absorbing EGFP with quantum yield 0.60 (Patterson, G., et al., J. Cell. Sci. (2001) 114:837-838).

The results of a gel-filtration test indicated that ppluGFP2 is monomeric protein since it demonstrated the same mobility as EGFP. Purified protein samples (~1 mg/ml) were loaded onto a Sephadex-100 column (0.7×60 cm) and eluted with a solution of 50 mM phosphate buffer (pH 7.0) and 100 mM NaCl. EGFP, HcRed1 and DsRed2 (Clontech) were used as monomer, dimer and tetramer standards, respectively.

Example 3

Preparation of ppluGFP2 Mutants and Derivates

The wild type ppluGFP2 nucleic acid coding sequence was obtained as described above in the Example 1. To enhance expression in mammalian cells we synthesized "humanized" version of ppluGFP2 using mammalian-optimised codons (SEQ ID NOs: 17 and 18). To enhance expression in *Saccharomyces cerevisiae* yeast-optimized version of ppluGFP2 was synthesized using *S. cerevisiae*-optimised codons (SEQ ID NOs: 19 and 20).

Figure 9:
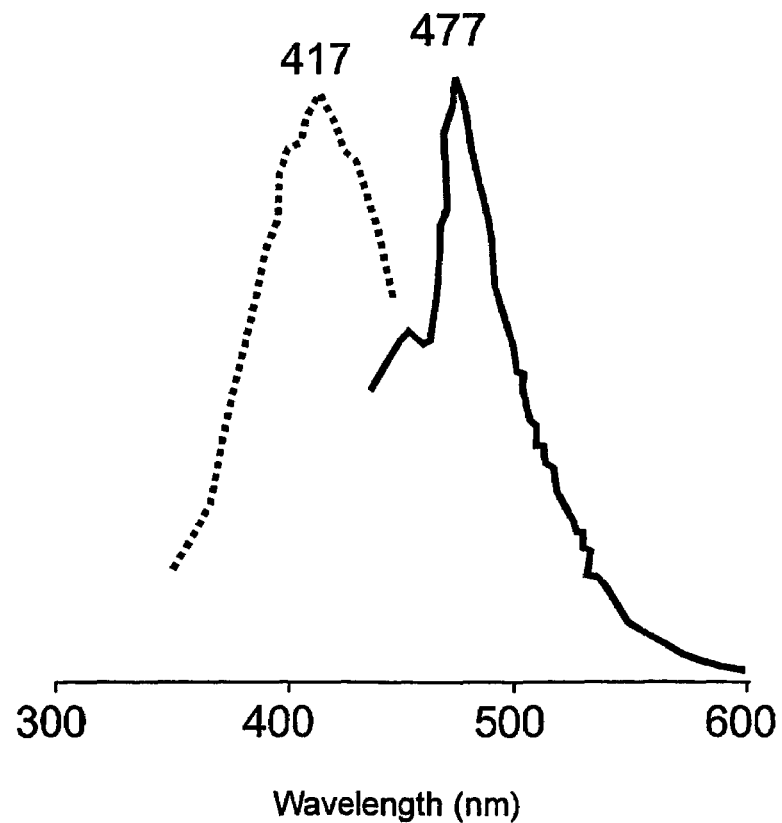
FIG. 9 illustrates the excitation (dashed line) and emission (solid line) spectra for CopCFP.

"Humanized" version of ppluGFP2 was subjected for site directed mutagenesis to obtain cyan light emitting versions of the protein. The mutant nucleic acid encoding protein with substitution Y58W was used for further random mutagenesis to improve maturation speed and brightness of fluorescence of the protein. The Diversity PCR Random Mutagenesis kit (CLONTECH) was used, under conditions optimal for 5-6 mutations per 1000 bp. *E. coli* colonies expressing mutant proteins were visually screened with a fluorescent stereomicroscope SZX-12 (Olympus). The brightest clone CopCFP was characterized further. Totally, this mutant carried 3 substitutions: Y58W, H143R, I119T (SEQ ID NOs: 21 and 22). Excitation-emission spectra for this protein possessed peaks at 417 and 477 nm, respectively (FIG. 9).

As ppluGFP2 displayed tendency to form aggregates both in solution in vitro and when expressed alone in long-term cell cultures, we generate the elongated versions of the protein with depressed ability to aggregate. The humanized version of the ppluGFP2 was used as template for non-aggregated variants generation. The first version (CopGFP-NA1, SEQ ID NOs: 23 and 24) contains K5E substitution (numbering is based on wild type) and elongated negatively charged amino acid tail at N-terminus of the protein that shields the positive charge on the outside interface of the ppluGFP2 barrel and prevents charge interaction with another ppluGFP2 protein molecule. The second version (CopGFP-NA2, SEQ ID NOs: 25 and 26) contains additional tail at C-terminus. The third variant, CopGFP-NA3, comprise all changes present in CopGFP-NA1 and CopGFP-NA2 versions (SEQ ID NOs: 27 and 28). All versions display reduced ability to aggregate in in vivo and in vitro tests.

Example 4

Polyclonal Antibody Preparation

Coding regions of nucleic acids of ppluGFP2 prepared as described above in the Examples 1 was cloned into pQE30 expressing vector (Qiagen), so that recombinant protein contained six-histidine tag at its N-terminus. After expression in *E. coli*, protein was purified by metal-affinity resin TALON (Clontech) under denaturing conditions. Rabbits were immunized and boosted four times at monthly intervals with recombinant polypeptides emulsified in complete Freund's adjuvant Ten or 11 days after each boost the animals were bled.

Polyclonal antiserum was tested on recombinant protein by ELISA and by Western immunobloting.

Example 5

Mammalian Cell Labeling Using ppluGFP2

For fluorescent labelling of eukaryotic cells, the humanised versions of ppluGFP2 prepared as described above in the Examples 3 was cloned into pEGFP-C1 vector (CLON-TECH) between AgeI and BglII restriction sites (in lieu of the EGFP-coding region). The following cell lines were used: 293T human kidney epithelial cells, 3T3 mouse embryo fibroblasts, L929 murine subcutaneous fibroblasts, Vero African green monkey kidney epithelial cells and COS1 African green monkey kidney fibroblasts. Cells were transfected using LipofectAMINE reagent (Invitrogen) and were tested 20 h after transfection. An Olympus CK40 fluorescence microscope equipped with a CCD camera (DP-50, Olympus) was used for cell imaging. Expression of ppluGFP2 in different cell lines resulted in bright green signals. Fluorescence was clearly detectable 24 hours after transfection. No cell toxicity was observed.

Example 6

Protein Labeling and Protein Localization Analysis Using ppluGFP2

The humanised versions of ppluGFP2 prepared as described above in the Examples 3 was fused to human cytoplasmic beta-actin and human nucleolar protein, fibrillarin. Transfection of 293T human kidney epithelial cells with plasmids expressing ppluGFP2-tagged fused constructs resulted in bright fluorescence that revealed pattern characteristic for the correspondent fusion partners.

Example 7

Cell Organelle Labeling Using ppluGFP2

The humanised versions of ppluGFP2 prepared as described above in the Examples 3 was fused to the following subcellular localization signals: mitochondrial targeting sequence (MTS) from subunit VIII of human cytochrome c oxidase; sequence encoding the N-terminal 81 amino acids of human beta 1,4-galactosyltransferase (GT; Watzele & Berger (1990) Nucleic Acids. Res. 18:7174); peroximal targeting signal 1 (Gould et al. J. Biol. Chem. (1989) 108: 1657-1664; Gould et al. EMBO J. (1990) 9: 85-90; Monosov et al. J. Histo. Cytochem. (1996) 44: 581-589); three copies of the nuclear localization signal (NLS) of the simian virus 40 large T-antigen fused at its C-terminus (Kalderon et al. Cell (1984) 39: 499-509; Lanford et al. Cell (1986) 46: 575-582).

Transfection of 293T human kidney epithelial cells with plasmids expressing ppluGFP2 tagged fused constructs resulted in effective translocation of the protein to the correspondent organelle of host cells. Fluorescence was clearly detectable 24 hours after transfection.

All publications and patent applications cited in this specification are incorporated by reference herein as if each individual publication or patent application were specifically and individually indicated to be incorporated by reference. The citation of any publication is to provide context and understanding of the present invention and should not be construed as an admission that any such publication is prior art.

What is claimed is:

1. An isolated nucleic acid molecule that encodes a fluorescent protein, wherein the nucleic acid is selected from the group consisting of:
   (a) a nucleic acid that encodes a fluorescent protein comprising the amino acid sequence as shown in SEQ ID NOs: 4, 18, 20, 22, 24, 26, or 28; and
   (b) a nucleic acid that encodes a fluorescent protein that has at least about 80% sequence identity to the amino acid sequence of (a) above; and
   wherein the protein encoded by the nucleic acid exhibits fluorescence.

2. The nucleic acid molecule of claim 1, wherein said nucleic acid is isolated from an organism from a phylum Anthropoda.

3. The nucleic acid molecule of claim 1, wherein said nucleic acid is isolated from an organism from a subclass Copepoda.

4. The nucleic acid molecule of claim 1, wherein said nucleic acid is isolated from a family Pontellidae.

5. A vector comprising the nucleic acid molecule according to claim 1.

6. An expression cassette comprising (a) a transcriptional initiator region functional in an expression host; (b) the isolated nucleic acid molecule according to claim 1; and (c) a transcriptional termination region functional in the expression host.

7. An isolated cell or progeny thereof comprising the expression cassette according to claim 6 as part of an extrachromosomal element or integrated into the genome of a host cell as a result of introduction of said expression cassette into said host cell.

8. A stable cell line comprising the expression cassette according to claim 6 as part of an extrachromosomal element or integrated into the genome of a host cell as a result of introduction of said expression cassette into said host cell.

9. A nucleic acid molecule encoding a flourescent protein having a sequence that is substantially the same as, or identical to a nucleotide sequence of at least 300 residues in length of the nucleic acid molecule according to claim 1, wherein the protein encoded by the nucleic acid exhibits fluorescence.

10. A kit comprising the nucleic acid molecule according to claim 1.

11. An isolated transgenic cell or progeny thereof comprising the expression cassette according to claim 6 as part of an extra chromosomal element or integrated into the genome of a host cell as a result of introduction of said expression cassette into said host cell.

* * * * *

```
                           SEQUENCE LISTING

<160> NUMBER OF SEQ ID NOS: 30

<210> SEQ ID NO 1
<211> LENGTH: 1010
<212> TYPE: DNA
<213> ORGANISM: Pontellina plumata

<400> SEQUENCE: 1
agtctgctct ccaaaggata gacagtaaca ccaccaatat gcctgccatg aagattgagt      60
gccgcatcag tggaaccctg aacggagtgg tgtttgagct ggtcggaggt ggagaaggga     120
ttcctgagca gggacgtatg accaacaaga tgaagtctac caagggcgcc ttgacttct     180 cccctacct tctctctcat gtcatgggat acgggttcta ccactttggg acctatccca     240
gtgggtatga gaatcccttc ctgcatgccg ccaacaacgg ggggtacacc aacaccagga     300
ttgagaagta tgaggatgga ggagttcttc atgttagctt cagctacaga tatgaagcag     360
gcagggttat tgggatttc aaggttgtcg ggacaggatt ccctgaggac agtgtgatct     420
tcaccgacaa gatcatccgg tccaatgcta ccgtggagca cttgcaccca atgggagaca     480
acgttcttgt gggctccttc gcgagaacct tttccctgag ggatggaggc tactactcat     540
ttgtggttga cagccacatg cacttcaaga gtgccatcca cccatccatc ctccagaacg     600
gggggtccat gtttgccttc aggagagttg aggaacttca ctccaacact gaacttggca     660
ttgtagagta tcaacatgcc ttcaagactc ccacagcatt tgcctgaact agaaagtatc     720
aaatataaac agagtgacaa aggatctgtc gtcattctaa actttgtatg atttacaaat     780
```

```
aatgatttaa tggcaactcc caaaatagac ttgaattaat tgaaaaatca actaaacata    840
atccttgttg ctctgttgat atgaacgctt tctgacttgg accccggctt gaactgaccc    900
tgaaccacat cagacgaata acttgattct aaaattatat gaattttcaa acaaaacaat    960
ataatttgtt aatgtgtaat catcttgaat aaacatatca gagaactcac               1010
```

<210> SEQ ID NO 2
<211> LENGTH: 222
<212> TYPE: PRT
<213> ORGANISM: Pontellina plumata

<400> SEQUENCE: 2

```
Met Pro Ala Met Lys Ile Glu Cys Arg Ile Ser Gly Thr Leu Asn Gly
1               5                   10                  15

Val Val Phe Glu Leu Val Gly Gly Gly Glu Gly Ile Pro Glu Gln Gly
            20                  25                  30

Arg Met Thr Asn Lys Met Lys Ser Thr Lys Gly Ala Leu Thr Phe Ser
        35                  40                  45

Pro Tyr Leu Leu Ser His Val Met Gly Tyr Gly Phe Tyr His Phe Gly
    50                  55                  60

Thr Tyr Pro Ser Gly Tyr Glu Asn Pro Phe Leu His Ala Ala Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
            100                 105                 110

Asp Phe Lys Val Val Gly Thr Gly Phe Pro Glu Asp Ser Val Ile Phe
        115                 120                 125

Thr Asp Lys Ile Ile Arg Ser Asn Ala Thr Val Glu His Leu His Pro
    130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Ser Met Phe
            180                 185                 190

Ala Phe Arg Arg Val Glu Glu Leu His Ser Asn Thr Glu Leu Gly Ile
        195                 200                 205

Val Glu Tyr Gln His Ala Phe Lys Thr Pro Thr Ala Phe Ala
    210                 215                 220
```

<210> SEQ ID NO 3
<211> LENGTH: 1010
<212> TYPE: DNA
<213> ORGANISM: Pontellina plumata

<400> SEQUENCE: 3

```
agtctgctct ccaaaggata gacagtaaca ccaccaatat gcctgccatg aagattgagt     60
gccgcatcac gggaaccctg aacggagtgg agtttgagct ggtcggaggt ggagaaggga    120
ctcctgagca gggacgtatg accaacaaga tgaagtctac caagggcgcc ttgaccttct    180
ccccctacct tctctctcat gtcatgggat acgggttcta ccactttggt acctatccca    240
gtgggtatga aatcccttc ctgcatgcca tcaacaacgg ggggtacacc aacaccagga    300
ttgagaagta tgaggatgga ggagttcttc atgttagctt tagctacaga tatgaagcag    360
```

-continued

```
gcagggtgat tgggatttc aaggttgtcg ggacaggatt ccctgaggac agtgtgatct    420
tcaccgacaa gatcatccgg tccaatgcta ccgtggagca cttgcaccca atgggagaca    480
acgttcttgt gggctccttc gcagaaacct tttccctgag ggatggaggc tactactcat    540
ttgtggttga cagccacatg cacttcaaga gtgccatcca cccatccatc ctccagaacg    600
gggggcccat gtttgccttc aggagagttg aggaacttca ctccaacact gaacttggca    660
ttgtagagta tcaacatgcc ttcaagactc ccatagcatt tgcttaaact acaaagtatc    720
aaatattaac agattgacaa aggatatgtc gtcattctaa actttgtatg atttacaaat    780
aatgatttaa tgtcaaccct caaaataggc ttgaattaat tgaaaaatca actaaacata    840
atccttgttg ctctgttgat atgaacactt tctgacttgg accccggctt gaactgaccc    900
tgacccacat cagacgaaga acttgattct aagattatat gaattttcaa aaaaaacaat    960
atgatttgtt aatgtgtaat catcttgaat aaacatatca gagaacgcac             1010
```

<210> SEQ ID NO 4
<211> LENGTH: 222
<212> TYPE: PRT
<213> ORGANISM: Pontellina plumata

<400> SEQUENCE: 4

```
Met Pro Ala Met Lys Ile Glu Cys Arg Ile Thr Gly Thr Leu Asn Gly
1               5                   10                  15

Val Glu Phe Glu Leu Val Gly Gly Gly Glu Gly Thr Pro Glu Gln Gly
            20                  25                  30

Arg Met Thr Asn Lys Met Lys Ser Thr Lys Gly Ala Leu Thr Phe Ser
        35                  40                  45

Pro Tyr Leu Leu Ser His Val Met Gly Tyr Gly Phe Tyr His Phe Gly
    50                  55                  60

Thr Tyr Pro Ser Gly Tyr Glu Asn Pro Phe Leu His Ala Ile Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
            100                 105                 110

Asp Phe Lys Val Val Gly Thr Gly Phe Pro Glu Asp Ser Val Ile Phe
        115                 120                 125

Thr Asp Lys Ile Ile Arg Ser Asn Ala Thr Val Glu His Leu His Pro
    130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Pro Met Phe
            180                 185                 190

Ala Phe Arg Arg Val Glu Glu Leu His Ser Asn Thr Glu Leu Gly Ile
        195                 200                 205

Val Glu Tyr Gln His Ala Phe Lys Thr Pro Ile Ala Phe Ala
    210                 215                 220
```

<210> SEQ ID NO 5
<211> LENGTH: 814
<212> TYPE: DNA
<213> ORGANISM: Labidocera aestiva

<400> SEQUENCE: 5

```
cagtttcttc caagctaaat aaagaaacac atcaaaagca tcaacatgcc tgtcatgaag      60
attgagtgcc gtatctctgg aaccatgaac ggagaggagt ttgagcttgt aggagctggc     120
gatggaaaca ctgatgaagg acgtatgacc aacaagatga agtccaccaa aggacctctc     180
tccttctctc cctacctact ctcccacatc atgggctacg gattctatca ctatgctacc     240
ttccctgctg gatatgagaa tgtctacctc catgctgcta agaatggagg ctacaccaac     300
accaggactg agaggtacga gacggagga atcatttcgg tcaacttcac ctacagatat      360
gagggaaaca aggttatcgg agacttcaag gttgttggat caggattccc agctaacagt     420
gttatcttca ctgacaagat catcaagtcc aacccaacct gtgagcacat ctaccccaag     480
ggagataata ttcttgtcaa tgcctacact cgaacttgga tgctgagaga tggtggatac     540
tactctgcac aggtcaacaa tcatctccac ttcaagactg ccatgcatcc caccatgctc     600
cagaacggag gatccatgtt tacctacagg aaggttgagg agctccacag ccagtcagat     660
gttggtattg tagaatacca acatgtcttc aagaccccaa ctgcttttgc ctaagcttgg     720
aaatatggtt cctatcagac aattaataca ataaacttta cttatcattg taaaaccaaa     780
ctcttttaat gaataaattt ctgtatctac tact                                 814
```

<210> SEQ ID NO 6
<211> LENGTH: 222
<212> TYPE: PRT
<213> ORGANISM: Labidocera aestiva

<400> SEQUENCE: 6

```
Met Pro Val Met Lys Ile Glu Cys Arg Ile Ser Gly Thr Met Asn Gly
1               5                   10                  15

Glu Glu Phe Glu Leu Val Gly Ala Gly Asp Gly Asn Thr Asp Glu Gly
            20                  25                  30

Arg Met Thr Asn Lys Met Lys Ser Thr Lys Gly Pro Leu Ser Phe Ser
        35                  40                  45

Pro Tyr Leu Leu Ser His Ile Met Gly Tyr Gly Phe Tyr His Tyr Ala
    50                  55                  60

Thr Phe Pro Ala Gly Tyr Glu Asn Val Tyr Leu His Ala Ala Lys Asn
65                  70                  75                  80

Gly Gly Tyr Thr Asn Thr Arg Thr Glu Arg Tyr Glu Asp Gly Gly Ile
                85                  90                  95

Ile Ser Val Asn Phe Thr Tyr Arg Tyr Glu Gly Asn Lys Val Ile Gly
            100                 105                 110

Asp Phe Lys Val Val Gly Ser Gly Phe Pro Ala Asn Ser Val Ile Phe
        115                 120                 125

Thr Asp Lys Ile Ile Lys Ser Asn Pro Thr Cys Glu His Ile Tyr Pro
    130                 135                 140

Lys Gly Asp Asn Ile Leu Val Asn Ala Tyr Thr Arg Thr Trp Met Leu
145                 150                 155                 160

Arg Asp Gly Gly Tyr Tyr Ser Ala Gln Val Asn Asn His Leu His Phe
                165                 170                 175

Lys Thr Ala Met His Pro Thr Met Leu Gln Asn Gly Gly Ser Met Phe
            180                 185                 190

Thr Tyr Arg Lys Val Glu Glu Leu His Ser Gln Ser Asp Val Gly Ile
        195                 200                 205

Val Glu Tyr Gln His Val Phe Lys Thr Pro Thr Ala Phe Ala
    210                 215                 220
```

<210> SEQ ID NO 7
<211> LENGTH: 753
<212> TYPE: DNA
<213> ORGANISM: cf. Pontella meadi Wheeler

<400> SEQUENCE: 7

```
atcagttcat cagtacacga gcagagtcac acatcaaaat gcctgacatg aagcttgagt      60
gccacatctc cggaaccatg aatggagagg agtttgaact tattggtgct ggagatggaa     120
atacagatga gggacgcatg accaacaaaa tgaagtccat caaaggacct atctccttct     180
ctccctacct cctctcccac attcttggct acggatatta ccactttgca accttccctg     240
ctggatatga aaatatctac cttcatgcca tgaagaatgg aggttactcc aatgtcagaa     300
ctgagaggta tgaggatgga ggcatcattt ctataacctt caactacaga tatgaaggga     360
acaagatcat tggagacttc aaggttgttg gaacaggatt ccctaccaac agtcttatct     420
tcactgacaa gatcattaaa tccaacccta cctgtgagaa catgttcccc aaggctgaca     480
atactcttgt gaatgcctac accagaacat atttgcttaa agatggtgga tactactctg     540
cccaggttaa caaccatatg cacttcaaga gtgccatcca taccaccatg ctccagaatg     600
gcggatccat gttcacctac agagttgtag aggagacaca cactcagaac gaagttgcta     660
ttgtagagta ccaaaatgtc ttcaaaactc caactgcgtt tgcttgaaat acttgtaata     720
aaactgcaaa gaaataaact aaattgtaca atc                                  753
```

<210> SEQ ID NO 8
<211> LENGTH: 222
<212> TYPE: PRT
<213> ORGANISM: cf. Pontella meadi Wheeler

<400> SEQUENCE: 8

Met Pro Asp Met Lys Leu Glu Cys His Ile Ser Gly Thr Met Asn Gly
1               5                   10                  15

Glu Glu Phe Glu Leu Ile Gly Ala Gly Asp Gly Asn Thr Asp Glu Gly
            20                  25                  30

Arg Met Thr Asn Lys Met Lys Ser Ile Lys Gly Pro Ile Ser Phe Ser
        35                  40                  45

Pro Tyr Leu Leu Ser His Ile Leu Gly Tyr Gly Tyr Tyr His Phe Ala
    50                  55                  60

Thr Phe Pro Ala Gly Tyr Glu Asn Ile Tyr Leu His Ala Met Lys Asn
65                  70                  75                  80

Gly Gly Tyr Ser Asn Val Arg Thr Glu Arg Tyr Glu Asp Gly Gly Ile
                85                  90                  95

Ile Ser Ile Thr Phe Asn Tyr Arg Tyr Glu Gly Asn Lys Ile Ile Gly
            100                 105                 110

Asp Phe Lys Val Val Gly Thr Gly Phe Pro Thr Asn Ser Leu Ile Phe
        115                 120                 125

Thr Asp Lys Ile Ile Lys Ser Asn Pro Thr Cys Glu Asn Met Phe Pro
    130                 135                 140

Lys Ala Asp Asn Thr Leu Val Asn Ala Tyr Thr Arg Thr Tyr Leu Leu
145                 150                 155                 160

Lys Asp Gly Gly Tyr Tyr Ser Ala Gln Val Asn Asn His Met His Phe
                165                 170                 175

Lys Ser Ala Ile His Thr Thr Met Leu Gln Asn Gly Gly Ser Met Phe
            180                 185                 190

Thr Tyr Arg Val Val Glu Glu Thr His Thr Gln Asn Glu Val Ala Ile

```
                195                 200                 205
Val Glu Tyr Gln Asn Val Phe Lys Thr Pro Thr Ala Phe Ala
    210                 215                 220

<210> SEQ ID NO 9
<211> LENGTH: 880
<212> TYPE: DNA
<213> ORGANISM: cf. Pontella meadi Wheeler

<400> SEQUENCE: 9
tcctgtgttc cagtcattac cgggccctgt gaggaggaag agcacacaga caggagagta      60
taaatacaga gcggaagcac ggtgatcatc agttcctcag taaacgagta gagacacaca     120
tcaaaatgcc tgacatgaag cttgagtgcc acatctccgg aaccatgaat ggagaggagt     180
ttgaacttat tggttctgga gatggaaata ctgatcaggg acgcatgaca aacaatatga     240
agtccatcaa aggacctctc tccttctctc cctacctact ctcccacatt cttggctatg     300
gatattacca ctttgcaacc ttccctgctg gatatgaaaa tatctacctt catgccatga     360
agaatggagg ttactcaaat gtcaggactg agaggtatga ggatggaggc atcattttcta    420 taaccttcaa ctacagatat gaaggcagca agatcattgg agacttcaaa gttattggaa     480
caggattccc taccgacagt cttatcttca ctgacaagat cattaaatcc aaccctacct     540
gcgagaacat gttccccaag gctgacaaca ttcttgtgaa tgcctacacc agaacctatt     600
tgcttaaaga tggtggatac tactctgccc aggttaacaa ccatatgcac ttcaagagtg     660
ccatccatcc tacaatgctc cagaatggtg gatccatgtt cactcacaga gtagtagagg     720
agaaccacac taagaccaac gttgctatcg tagagtacca aatgtcttc aaaactccta     780 ctgcatttgc ttaaaatact tgtaacaaaa ctgcaaagaa ataacctata ttgtacaata     840 gcatttatt aatgcataga aaataaatg tatattttat                             880

<210> SEQ ID NO 10
<211> LENGTH: 222
<212> TYPE: PRT
<213> ORGANISM: cf. Pontella meadi Wheeler

<400> SEQUENCE: 10

Met Pro Asp Met Lys Leu Glu Cys His Ile Ser Gly Thr Met Asn Gly
1               5                   10                  15

Glu Glu Phe Glu Leu Ile Gly Ser Gly Asp Gly Asn Thr Asp Gln Gly
            20                  25                  30

Arg Met Thr Asn Asn Met Lys Ser Ile Lys Gly Pro Leu Ser Phe Ser
        35                  40                  45

Pro Tyr Leu Leu Ser His Ile Leu Gly Tyr Gly Tyr Tyr His Phe Ala
    50                  55                  60

Thr Phe Pro Ala Gly Tyr Glu Asn Ile Tyr Leu His Ala Met Lys Asn
65                  70                  75                  80

Gly Gly Tyr Ser Asn Val Arg Thr Glu Arg Tyr Glu Asp Gly Gly Ile
                85                  90                  95

Ile Ser Ile Thr Phe Asn Tyr Arg Tyr Glu Gly Ser Lys Ile Ile Gly
            100                 105                 110

Asp Phe Lys Val Ile Gly Thr Gly Phe Pro Thr Asp Ser Leu Ile Phe
        115                 120                 125

Thr Asp Lys Ile Ile Lys Ser Asn Pro Thr Cys Glu Asn Met Phe Pro
    130                 135                 140

Lys Ala Asp Asn Ile Leu Val Asn Ala Tyr Thr Arg Thr Tyr Leu Leu
```

```
            145                 150                 155                 160
Lys Asp Gly Gly Tyr Tyr Ser Ala Gln Val Asn Asn His Met His Phe
                    165                 170                 175

Lys Ser Ala Ile His Pro Thr Met Leu Gln Asn Gly Gly Ser Met Phe
            180                 185                 190

Thr His Arg Val Val Glu Glu Asn His Thr Lys Thr Asn Val Ala Ile
        195                 200                 205

Val Glu Tyr Gln Asn Val Phe Lys Thr Pro Thr Ala Phe Ala
    210                 215                 220

<210> SEQ ID NO 11
<211> LENGTH: 847
<212> TYPE: DNA
<213> ORGANISM: Pontella mediterranea

<400> SEQUENCE: 11
agcagtggta tcaacgcaga gtacgcggga gttcctcaac gaaaaccaag agaaacagac      60
atcaagatgc ccaacatgaa gcttgagtgc cgtatctccg gaaccatgaa tggagaggag     120
tttgaacttg ttggtgctgg agaaggaaac actgatgagg acgcatgac caacaagatg      180 aagtccacca agggacctct tccttctct ccttatttgc tctcccacgt tcttggttat      240
ggatactacc actatgctac cttccctgct ggatatgaaa atgtctacct ccatgccatg     300
aagaatggag gttactccaa cacaagaact gagaggtatg aggatggagg tatcatttct     360
gctaccttca actacagata tgaagggaga cagattcatg gagacttcaa ggttgtagga     420
acgggattcc ctgccgacag catcatcttc actgacaaga tcatcaagtc caaccctacc     480
tgtgagcaca tctaccccaa ggctaacaat attcttgtga atgcttacac agaacctgg      540 atgcttagag atggtggata ctactctgcc caggtcaaca accacatgca tttacagagt     600
gccattcatc ccaccatgct caagaatggt ggatctatgt tcacctacag aaaggttgag     660
gagctccaca cacaaactga agtcggtatt gttgaatacc agcatgtctt caagaggcca     720
actgcttttg cttaattttg taataaaga aagaatctat aatgcaatag taccttaaag      780
ttttcaggat aataaatata taaagatttt taataaaaaa aaaaaaaaaa aaaaaaaaa      840 aaaaaaa                                                               847

<210> SEQ ID NO 12
<211> LENGTH: 222
<212> TYPE: PRT
<213> ORGANISM: Pontella mediterranea

<400> SEQUENCE: 12

Met Pro Asn Met Lys Leu Glu Cys Arg Ile Ser Gly Thr Met Asn Gly
1               5                   10                  15

Glu Glu Phe Glu Leu Val Gly Ala Gly Glu Gly Asn Thr Asp Glu Gly
                20                  25                  30

Arg Met Thr Asn Lys Met Lys Ser Thr Lys Gly Pro Leu Ser Phe Ser
            35                  40                  45

Pro Tyr Leu Leu Ser His Val Leu Gly Tyr Gly Tyr Tyr His Tyr Ala
        50                  55                  60

Thr Phe Pro Ala Gly Tyr Glu Asn Val Tyr Leu His Ala Met Lys Asn
65                  70                  75                  80

Gly Gly Tyr Ser Asn Thr Arg Thr Glu Arg Tyr Glu Asp Gly Gly Ile
                85                  90                  95

Ile Ser Ala Thr Phe Asn Tyr Arg Tyr Glu Gly Arg Gln Ile His Gly
```

-continued

```
                100                 105                 110
Asp Phe Lys Val Val Gly Thr Gly Phe Pro Ala Asp Ser Ile Ile Phe
            115                 120                 125

Thr Asp Lys Ile Ile Lys Ser Asn Pro Thr Cys Glu His Ile Tyr Pro
145             150                 155                 160

Lys Ala Asn Asn Ile Leu Val Asn Ala Tyr Thr Arg Thr Trp Met Leu
145             150                 155                 160

Arg Asp Gly Gly Tyr Tyr Ser Ala Gln Val Asn Asn His Met His Leu
                165                 170                 175

Gln Ser Ala Ile His Pro Thr Met Leu Lys Asn Gly Gly Ser Met Phe
            180                 185                 190

Thr Tyr Arg Lys Val Glu Glu Leu His Thr Gln Thr Glu Val Gly Ile
                195                 200                 205

Val Glu Tyr Gln His Val Phe Lys Arg Pro Thr Ala Phe Ala
            210                 215                 220
```

<210> SEQ ID NO 13
<211> LENGTH: 850
<212> TYPE: DNA
<213> ORGANISM: Pontella mediterranea

<400> SEQUENCE: 13

```
gcagtggtat caacgcagag tacgcgggga gttcctcaac gaaaaccgag agaaacatac      60
atcaaaatgc cccacatgaa gcttgagtgc cgtatctccg gaaccatgaa cggagaggag     120
tttgaacttg ttggtgctgg agatggaaac actgatgagg gacgcatgac caaccagatg     180
aagtccacaa agggacctct ctccttctct ccctacttgc tctcccacgt tcttggctat     240
ggatactacc actatgctac cttccctgct ggatatgaaa atgtctacct ccatgccatg     300
aagaatggag gttactccaa cacaagaact gagaggtatg acgatggagg tatcattcct     360
gctaccttca actacagata tgaagggaga cagattcatg gagacttcaa ggttgttgga     420
actggattcc ctgccgacag catcatcttc actgacaaga tcatcaagtc caaccctacc     480
tgtgagcaca tctaccccaa ggctgacaat attcttgtga atgcctacac agaacctgg      540
atgcttagag atggtggata ctactctgct caggtcaaca accacatgca ctttaagagt     600
gccatccatc ccaccatgct ccagaatggt ggatctatgt tcacctacag aaaggttgag     660
gagctccaca cacaaactga agttggtatt gttgagtacc agcatgtttt caagaggccc     720
acagcttttg cttaattttg taaataaaga aagaatttat aatacaatag tgcttttatg     780
tttctaaaac aatgaatgta taaataaatc tcaaatatt caaaaaaaaa aaaaaaaaaa      840
aaaaaaaaaa                                                            850
```

<210> SEQ ID NO 14
<211> LENGTH: 222
<212> TYPE: PRT
<213> ORGANISM: Pontella mediterranea

<400> SEQUENCE: 14

```
Met Pro His Met Lys Leu Glu Cys Arg Ile Ser Gly Thr Met Asn Gly
1               5                   10                  15

Glu Glu Phe Glu Leu Val Gly Ala Gly Asp Gly Asn Thr Asp Glu Gly
            20                  25                  30

Arg Met Thr Asn Gln Met Lys Ser Thr Lys Gly Pro Leu Ser Phe Ser
                35                  40                  45

Pro Tyr Leu Leu Ser His Val Leu Gly Tyr Gly Tyr Tyr His Tyr Ala
```

```
                50                  55                  60
Thr Phe Pro Ala Gly Tyr Glu Asn Val Tyr Leu His Ala Met Lys Asn
 65                  70                  75                  80

Gly Gly Tyr Ser Asn Thr Arg Thr Glu Arg Tyr Asp Asp Gly Gly Ile
                 85                  90                  95

Ile Ser Ala Thr Phe Asn Tyr Arg Tyr Glu Gly Arg Gln Ile His Gly
                100                 105                 110

Asp Phe Lys Val Val Gly Thr Gly Phe Pro Ala Asp Ser Ile Ile Phe
            115                 120                 125

Thr Asp Lys Ile Ile Lys Ser Asn Pro Thr Cys Glu His Ile Tyr Pro
    130                 135                 140

Lys Ala Asp Asn Ile Leu Val Asn Ala Tyr Thr Arg Thr Trp Met Leu
145                 150                 155                 160

Arg Asp Gly Gly Tyr Tyr Ser Ala Gln Val Asn Asn His Met His Phe
                165                 170                 175

Lys Ser Ala Ile His Pro Thr Met Leu Gln Asn Gly Ser Met Phe
            180                 185                 190

Thr Tyr Arg Lys Val Glu Glu Leu His Thr Gln Thr Glu Val Gly Ile
        195                 200                 205

Val Glu Tyr Gln His Val Phe Lys Arg Pro Thr Ala Phe Ala
    210                 215                 220
```

<210> SEQ ID NO 15
<211> LENGTH: 821
<212> TYPE: DNA
<213> ORGANISM: Unknown
<220> FEATURE:
<223> OTHER INFORMATION: unidentified Pontellidae species

<400> SEQUENCE: 15

```
atcagtttaa cttctttcag aagacaacta agacctacca acatggcagc catgaagatt    60
gagtgcagga tcactggaac catgaacgga gtggagtttg agctggttgg aggaggagaa   120
ggaaatactg atcagggacg tatgaccaac aagatgaaat ctaccaaggg tccactctcc   180
ttctctccct atcttctctc tcatgtcatg ggatatggat tctatcattt tggaacattt   240
cccagtggtt atgagaatcc ctatgtccac gccatgacga acggtggata taccaacacc   300
aggattgaaa gttatgaaga tggaggtgtt ctttacctta ccttcaacta cagattggat   360
ggaaacaaga ttatcgggga cttcaagtgt gtcggaactg gattccctga ggacagcgtt   420
atcttcactg acaagatcat caagtccaac cccaattgtg aacatttcta tccaatggct   480
gaaaacatca tgaaaaatgc ctacatgaga actctctccc tcagagatgg tggctactac   540
tctggccagg ttaccagcca catccacttc aagaatgcga tccacccatc catccttcat   600
aacggcggat ccatgttcac ctacagaaga gttgaggagc tccacactca aactgatctt   660
ggaattgttg agtaccagca tgtattcaag actcccactg cttttgcttg aatgccatga   720
agatgaaacc tgaacaagat caatctttat ttaccacaat atgtaaattg tttaattgta   780
taattctcga gaattcatat aatacataga atttatctta c                       821
```

<210> SEQ ID NO 16
<211> LENGTH: 222
<212> TYPE: PRT
<213> ORGANISM: Unknown
<220> FEATURE:
<223> OTHER INFORMATION: unidentified Pontellidae species

<400> SEQUENCE: 16

```
Met Ala Ala Met Lys Ile Glu Cys Arg Ile Thr Gly Thr Met Asn Gly
1               5                   10                  15

Val Glu Phe Glu Leu Val Gly Gly Glu Gly Asn Thr Asp Gln Gly
            20                  25                  30

Arg Met Thr Asn Lys Met Lys Ser Thr Lys Gly Pro Leu Ser Phe Ser
            35                  40                  45

Pro Tyr Leu Leu Ser His Val Met Gly Tyr Gly Phe Tyr His Phe Gly
        50                  55                  60

Thr Phe Pro Ser Gly Tyr Glu Asn Pro Tyr Val His Ala Met Thr Asn
65                  70                  75                  80

Gly Gly Tyr Thr Asn Thr Arg Ile Glu Ser Tyr Glu Asp Gly Gly Val
                85                  90                  95

Leu Tyr Leu Thr Phe Asn Tyr Arg Leu Asp Gly Asn Lys Ile Ile Gly
                100                 105                 110

Asp Phe Lys Cys Val Gly Thr Gly Phe Pro Glu Asp Ser Val Ile Phe
            115                 120                 125

Thr Asp Lys Ile Ile Lys Ser Asn Pro Asn Cys Glu His Phe Tyr Pro
130                 135                 140

Met Ala Glu Asn Ile Met Lys Asn Ala Tyr Met Arg Thr Leu Ser Leu
145                 150                 155                 160

Arg Asp Gly Gly Tyr Tyr Ser Gly Gln Val Thr Ser His Ile His Phe
                165                 170                 175

Lys Asn Ala Ile His Pro Ser Ile Leu His Asn Gly Gly Ser Met Phe
            180                 185                 190

Thr Tyr Arg Arg Val Glu Glu Leu His Thr Gln Thr Asp Leu Gly Ile
        195                 200                 205

Val Glu Tyr Gln His Val Phe Lys Thr Pro Thr Ala Phe Ala
        210                 215                 220

<210> SEQ ID NO 17
<211> LENGTH: 669
<212> TYPE: DNA
<213> ORGANISM: Artificial Sequence
<220> FEATURE:
<223> OTHER INFORMATION: nucleic acid sequence for humanized version of
      ppluGFP2

<400> SEQUENCE: 17
atgcccgcca tgaagatcga gtgccgcatc accggcaccc tgaacggcgt ggagttcgag      60
ctggtgggcg gcggagaggg caccccccgag cagggccgca tgaccaacaa gatgaagagc     120
accaagggcg ccctgacctt cagcccctac ctgctgagcc acgtgatggg ctacggcttc     180
taccacttcg gcacctaccc cagcggctac gagaacccct cctgcacgc catcaacaac      240 ggcggctaca ccaacacccg catcgagaag tacgaggacg gcggcgtgct gcacgtgagc     300
ttcagctacc gctacgaggc cggccgcgtg atcggcgact caaggtggt gggcaccggc      360 ttccccgagg acagcgtgat cttcaccgac aagatcatcc gcagcaacgc caccgtggag     420
cacctgcacc ccatgggcga taacgtgctg gtgggcagct cgcccgcac cttcagcctg      480 cgcgacggcg gctactacag cttcgtggtg gacagccaca tgcacttcaa gagcgccatc     540 cacccccagca tcctgcagaa cggggggcccc atgttcgcct ccgccgcgt ggaggagctg    600 cacagcaaca ccgagctggg catcgtggag taccagcacg ccttcaagac cccgatcgca     660
ttcgcctga                                                            669
```

<210> SEQ ID NO 18
<211> LENGTH: 222
<212> TYPE: PRT
<213> ORGANISM: Artificial Sequence
<220> FEATURE:
<223> OTHER INFORMATION: polypeptide sequence for humanized version of ppluGFP2

<400> SEQUENCE: 18

```
Met Pro Ala Met Lys Ile Glu Cys Arg Ile Thr Gly Thr Leu Asn Gly
1               5                   10                  15

Val Glu Phe Glu Leu Val Gly Gly Gly Glu Gly Thr Pro Glu Gln Gly
            20                  25                  30

Arg Met Thr Asn Lys Met Lys Ser Thr Lys Gly Ala Leu Thr Phe Ser
        35                  40                  45

Pro Tyr Leu Leu Ser His Val Met Gly Tyr Gly Phe Tyr His Phe Gly
    50                  55                  60

Thr Tyr Pro Ser Gly Tyr Glu Asn Pro Phe Leu His Ala Ile Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
            100                 105                 110

Asp Phe Lys Val Val Gly Thr Gly Phe Pro Glu Asp Ser Val Ile Phe
        115                 120                 125

Thr Asp Lys Ile Ile Arg Ser Asn Ala Thr Val Glu His Leu His Pro
    130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Pro Met Phe
            180                 185                 190

Ala Phe Arg Arg Val Glu Glu Leu His Ser Asn Thr Glu Leu Gly Ile
        195                 200                 205

Val Glu Tyr Gln His Ala Phe Lys Thr Pro Ile Ala Phe Ala
    210                 215                 220
```

<210> SEQ ID NO 19
<211> LENGTH: 589
<212> TYPE: DNA
<213> ORGANISM: Artificial Sequence
<220> FEATURE:
<223> OTHER INFORMATION: nucleic acid sequence for ppluGFP2 with yeast-optimized codon usage

<400> SEQUENCE: 19

```
tactccagaa caaggtagaa tgactaataa aatgaaatct actaaaggtg ctttgacttt      60
ttctccatat ttgttgtctc atgttatggg ttatggtttt tatcattttg gtacttatcc     120
atctggttat gaaaatccat ttttgcatgc tattaataat ggtggttata ctaatactag     180
aattgaaaaa tatgaagatg gtggtgtttt gcatgtttct ttttcttata gatatgaagc     240
tggtagagtt attggcgatt ttaaagttgt tggtactggt tttccagaag attctgttat     300
ttttactgat aaaattatta gatctaatgc tactgttgaa catttgcatc caatgggtga     360
taatgttttg gttggttctt ttgctagaac ttttttcttg agagatggtg gttattattc     420
ttttgttgtt gattctcata tgcatttaa atctgctatt catccatcta ttttgcaaaa     480
```

```
tggtggtcca atgtttgctt ttagaagagt tgaagaattg cattctaata ctgaattggg     540
tattgttgaa tatcaacatg cttttaaaac tccaattgct tttgcttaa                 589
```

<210> SEQ ID NO 20
<211> LENGTH: 222
<212> TYPE: PRT
<213> ORGANISM: Artificial Sequence
<220> FEATURE:
<223> OTHER INFORMATION: polypeptide sequence for ppluGFP2 with
      yeast-optimized codon usage

<400> SEQUENCE: 20

```
Met Pro Ala Met Lys Ile Glu Cys Arg Ile Thr Gly Thr Leu Asn Gly
1               5                   10                  15

Val Glu Phe Glu Leu Val Gly Gly Gly Glu Gly Thr Pro Glu Gln Gly
            20                  25                  30

Arg Met Thr Asn Lys Met Lys Ser Thr Lys Gly Ala Leu Thr Phe Ser
        35                  40                  45

Pro Tyr Leu Leu Ser His Val Met Gly Tyr Gly Phe Tyr His Phe Gly
    50                  55                  60

Thr Tyr Pro Ser Gly Tyr Glu Asn Pro Phe Leu His Ala Ile Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
            100                 105                 110

Asp Phe Lys Val Val Gly Thr Gly Phe Pro Glu Asp Ser Val Ile Phe
        115                 120                 125

Thr Asp Lys Ile Ile Arg Ser Asn Ala Thr Val Glu His Leu His Pro
    130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Pro Met Phe
            180                 185                 190

Ala Phe Arg Arg Val Glu Glu Leu His Ser Asn Thr Glu Leu Gly Ile
        195                 200                 205

Val Glu Tyr Gln His Ala Phe Lys Thr Pro Ile Ala Phe Ala
    210                 215                 220
```

<210> SEQ ID NO 21
<211> LENGTH: 669
<212> TYPE: DNA
<213> ORGANISM: Artificial Sequence
<220> FEATURE:
<223> OTHER INFORMATION: nucleic acid sequence for CopCFP mutant

<400> SEQUENCE: 21

```
atgcccgcca tgaagatcga gtgccgcatc accggcaccc tgaacggcgt ggagttcgag      60
ctggtgggcg gcggagaggg caccccccgag cagggccgca tgaccaacaa gatgaagagc    120
accaaaggcg ccctgacctt cagcccctac ctgctgagcc acgtgatggg ctggggcttt    180
taccacttcg gcacctaccc cagcggctac gagaacccct cctgcacgc catcaacaac     240 ggcggctaca ccaacacccg catcgagaag tacgaggacg gcggcgtgct gcacgtgagc    300
ttcagctacc gctacgaggc cggccgcgtg atcggcgact tcaaggtggt gggcaccggc    360
```

```
ttccccgagg acagcgtgat cttcaccgac aagatcatcc gcagcaacgc caccgtggag    420
cacctgcgcc ccatgggcga taacgtgctg gtgggcagct cgcccgcac cttcagcctg    480 cgcgacggcg gctactacag cttcgtggtg gacagccaca tgcacttcaa gagcgccatc    540
caccccagca tcctgcagaa cggggggccc catgttcgcc tccgccgcgt ggaggagctg    600
cacagcaaca ccgagctggg catcgtggag taccagcacg ccttcaagac cccgaccgca    660
ttcgcctaa                                                            669
```

<210> SEQ ID NO 22
<211> LENGTH: 222
<212> TYPE: PRT
<213> ORGANISM: Artificial Sequence
<220> FEATURE:
<223> OTHER INFORMATION: polypeptide sequence for CopCFP mutant
<400> SEQUENCE: 22

```
Met Pro Ala Met Lys Ile Glu Cys Arg Ile Thr Gly Thr Leu Asn Gly
1               5                   10                  15

Val Glu Phe Glu Leu Val Gly Gly Gly Glu Gly Thr Pro Glu Gln Gly
            20                  25                  30

Arg Met Thr Asn Lys Met Lys Ser Thr Lys Gly Ala Leu Thr Phe Ser
        35                  40                  45

Pro Tyr Leu Leu Ser His Val Met Gly Trp Gly Phe Tyr His Phe Gly
    50                  55                  60

Thr Tyr Pro Ser Gly Tyr Glu Asn Pro Phe Leu His Ala Ile Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
            100                 105                 110

Asp Phe Lys Val Val Gly Thr Gly Phe Pro Glu Asp Ser Val Ile Phe
        115                 120                 125

Thr Asp Lys Ile Ile Arg Ser Asn Ala Thr Val Glu His Leu Arg Pro
    130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Pro Met Phe
            180                 185                 190

Ala Phe Arg Arg Val Glu Glu Leu His Ser Asn Thr Glu Leu Gly Ile
        195                 200                 205

Val Glu Tyr Gln His Ala Phe Lys Thr Pro Thr Ala Phe Ala
    210                 215                 220
```

<210> SEQ ID NO 23
<211> LENGTH: 690
<212> TYPE: DNA
<213> ORGANISM: Artificial Sequence
<220> FEATURE:
<223> OTHER INFORMATION: nucleic acid sequence for CopGFP-NA1 mutant
<400> SEQUENCE: 23

```
atggagagcg acgagagcgg cctgcccgcc atggagatcg agtgccgcat caccggcacc     60
ctgaacggcg tggagttcga gctggtgggc ggcggagagg gcacccccga gcagggccgc    120
atgaccaaca agatgaagag caccaagggc gccctgacct tcagccccta cctgctgagc    180
```

```
cacgtgatgg gctacggctt ctaccacttc ggcacctacc ccagcggcta cgagaacccc      240
ttcctgcacg ccatcaacaa cggcggctac accaacaccc gcatcgagaa gtacgaggac      300
ggcggcgtgc tgcacgtgag cttcagctac cgctacgagg ccggccgcgt gatcggcgac      360
ttcaaggtgg tgggcaccgg cttccccgag gacagcgtga tcttcaccga caagatcatc      420
cgcagcaacg ccaccgtgga gcacctgcac cccatgggcg ataacgtgct ggtgggcagc      480
ttcgcccgca ccttcagcct gcgcgacggc ggctactaca gcttcgtggt ggacagccac      540
atgcacttca gagcgccat ccaccccagc atcctgcaga cgggggccc catgttcgcc       600 ttccgccgcg tggaggagct gcacagcaac accgagctgg gcatcgtgga gtaccagcac      660
gccttcaaga ccccgatcgc attcgcctga                                       690
```

<210> SEQ ID NO 24
<211> LENGTH: 229
<212> TYPE: PRT
<213> ORGANISM: Artificial Sequence
<220> FEATURE:
<223> OTHER INFORMATION: polypeptide sequence for CopGFP-NA1 mutant

<400> SEQUENCE: 24

```
Met Glu Ser Asp Glu Ser Gly Leu Pro Ala Met Glu Ile Glu Cys Arg
1               5                   10                  15

Ile Thr Gly Thr Leu Asn Gly Val Glu Phe Glu Leu Val Gly Gly Gly
                20                  25                  30

Glu Gly Thr Pro Glu Gln Gly Arg Met Thr Asn Lys Met Lys Ser Thr
            35                  40                  45

Lys Gly Ala Leu Thr Phe Ser Pro Tyr Leu Leu Ser His Val Met Gly
    50                  55                  60

Tyr Gly Phe Tyr His Phe Gly Thr Tyr Pro Ser Gly Tyr Glu Asn Pro
65                  70                  75                  80

Phe Leu His Ala Ile Asn Asn Gly Gly Tyr Thr Asn Thr Arg Ile Glu
                85                  90                  95

Lys Tyr Glu Asp Gly Gly Val Leu His Val Ser Phe Ser Tyr Arg Tyr
            100                 105                 110

Glu Ala Gly Arg Val Ile Gly Asp Phe Lys Val Val Gly Thr Gly Phe
        115                 120                 125

Pro Glu Asp Ser Val Ile Phe Thr Asp Lys Ile Ile Arg Ser Asn Ala
    130                 135                 140

Thr Val Glu His Leu His Pro Met Gly Asp Asn Val Leu Val Gly Ser
145                 150                 155                 160

Phe Ala Arg Thr Phe Ser Leu Arg Asp Gly Gly Tyr Tyr Ser Phe Val
                165                 170                 175

Val Asp Ser His Met His Phe Lys Ser Ala Ile His Pro Ser Ile Leu
            180                 185                 190

Gln Asn Gly Gly Pro Met Phe Ala Phe Arg Arg Val Glu Glu Leu His
        195                 200                 205

Ser Asn Thr Glu Leu Gly Ile Val Glu Tyr Gln His Ala Phe Lys Thr
    210                 215                 220

Pro Ile Ala Phe Ala
225
```

<210> SEQ ID NO 25
<211> LENGTH: 819
<212> TYPE: DNA
<213> ORGANISM: Artificial Sequence
<220> FEATURE:
<223> OTHER INFORMATION: nucleic acid sequence for CopGFP-NA2 mutant

<400> SEQUENCE: 25

```
atgcccgcca tgaagatcga gtgccgcatc accggcaccc tgaacggcgt ggagttcgag      60
ctggtgggcg gcggagaggg caccccccgag cagggccgca tgaccaacaa gatgaagagc    120
accaagggcg ccctgacctt cagccccctac ctgctgagcc acgtgatggg ctacggcttc    180
taccacttcg gcacctaccc cagcggctac gagaacccct tcctgcacgc catcaacaac    240
ggcggctaca ccaacacccg catcgagaag tacgaggacg gcggcgtgct gcacgtgagc    300
ttcagctacc gctacgaggc cggccgcgtg atcggcgact tcaaggtggt gggcaccggc    360
ttccccgagg acagcgtgat cttcaccgac aagatcatcc gcagcaacgc caccgtggag    420
cacctgcacc ccatgggcga taacgtgctg gtgggcagct tcgcccgcac cttcagcctg    480
cgcgacggcg gctactacag cttcgtggtg gacagccaca tgcacttcaa gagcgccatc    540
caccccagca tcctgcagaa cggggggcccc atgttcgcct tccgccgcgt ggaggagctg    600
cacagcaaca ccgagctggg catcgtggag taccagcacg ccttcaagac ccgatcgca    660
ttcgccagat ccagagccca ggccagcaac tccgccgtgg atggcacagc cggaccggga    720
tcggccgcga ctctagatca taatcagcca taccacattt gtagaggttt tacttgcttt    780
aaaaaacctc ccacacctcc ccctgaacct gaaacataa                           819
```

<210> SEQ ID NO 26
<211> LENGTH: 272
<212> TYPE: PRT
<213> ORGANISM: Artificial Sequence
<220> FEATURE:
<223> OTHER INFORMATION: polypeptide sequence for CopGFP-NA2 mutant

<400> SEQUENCE: 26

```
Met Pro Ala Met Lys Ile Glu Cys Arg Ile Thr Gly Thr Leu Asn Gly
1               5                   10                  15

Val Glu Phe Glu Leu Val Gly Gly Gly Glu Gly Thr Pro Glu Gln Gly
            20                  25                  30

Arg Met Thr Asn Lys Met Lys Ser Thr Lys Gly Ala Leu Thr Phe Ser
        35                  40                  45

Pro Tyr Leu Leu Ser His Val Met Gly Tyr Gly Phe Tyr His Phe Gly
    50                  55                  60

Thr Tyr Pro Ser Gly Tyr Glu Asn Pro Phe Leu His Ala Ile Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
            100                 105                 110

Asp Phe Lys Val Val Gly Thr Gly Phe Pro Glu Asp Ser Val Ile Phe
        115                 120                 125

Thr Asp Lys Ile Ile Arg Ser Asn Ala Thr Val Glu His Leu His Pro
    130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Pro Met Phe
            180                 185                 190
```

```
Ala Phe Arg Arg Val Glu Glu Leu His Ser Asn Thr Glu Leu Gly Ile
            195                 200                 205

Val Glu Tyr Gln His Ala Phe Lys Thr Pro Ile Ala Phe Ala Arg Ser
        210                 215                 220

Arg Ala Gln Ala Ser Asn Ser Ala Val Asp Gly Thr Ala Gly Pro Gly
225                 230                 235                 240

Ser Ala Ala Thr Leu Asp His Asn Gln Pro Tyr His Ile Cys Arg Gly
                245                 250                 255

Phe Thr Cys Phe Lys Lys Pro Pro Thr Pro Pro Glu Pro Glu Thr
            260                 265                 270
```

<210> SEQ ID NO 27
<211> LENGTH: 840
<212> TYPE: DNA
<213> ORGANISM: Artificial Sequence
<220> FEATURE:
<223> OTHER INFORMATION: nucleic acid sequence for CopGFP-NA3 mutant

<400> SEQUENCE: 27

```
atggagagcg acgagagcgg cctgcccgcc atggagatcg agtgccgcat caccggcacc    60
ctgaacggcg tggagttcga gctggtgggc ggcggagagg gcaccccga gcagggccgc    120
atgaccaaca agatgaagag caccaagggc gccctgacct tcagccccta cctgctgagc    180
cacgtgatgg gctacggctt ctaccacttc ggcacctacc ccagcggcta cgagaacccc    240
ttcctgcacg ccatcaacaa cggcggctac accaacaccc gcatcgagaa gtacgaggac    300
ggcggcgtgc tgcacgtgag cttcagctac cgctacgagg ccggccgcgt gatcggcgac    360
ttcaaggtgg tgggcaccgg cttccccgag gacagcgtga tcttcaccga caagatcatc    420
cgcagcaacg ccaccgtgga gcacctgcac cccatgggcg ataacgtgct ggtgggcagc    480
ttcgcccgca ccttcagcct gcgcgacggc ggctactaca gcttcgtggt ggacagccac    540
atgcacttca gagcgccat ccaccccagc atcctgcaga acggggcc catgttcgcc    600
ttccgccgcg tggaggagct gcacagcaac accgagctgg gcatcgtgga gtaccagcac    660
gccttcaaga cccgatcgc attcgccaga tccagagccc aggccagcaa ctccgccgtg    720
gatggcacag ccggaccggg atcggccgcg actctagatc ataatcagcc ataccacatt    780
tgtagaggtt ttacttgctt taaaaaacct cccacacctc cccctgaacc tgaaacataa    840
```

<210> SEQ ID NO 28
<211> LENGTH: 279
<212> TYPE: PRT
<213> ORGANISM: Artificial Sequence
<220> FEATURE:
<223> OTHER INFORMATION: polypeptide sequence for CopGFP-NA3 mutant

<400> SEQUENCE: 28

```
Met Glu Ser Asp Glu Ser Gly Leu Pro Ala Met Glu Ile Glu Cys Arg
1               5                   10                  15

Ile Thr Gly Thr Leu Asn Gly Val Glu Phe Glu Leu Val Gly Gly Gly
            20                  25                  30

Glu Gly Thr Pro Glu Gln Gly Arg Met Thr Asn Lys Met Lys Ser Thr
        35                  40                  45

Lys Gly Ala Leu Thr Phe Ser Pro Tyr Leu Leu Ser His Val Met Gly
    50                  55                  60

Tyr Gly Phe Tyr His Phe Gly Thr Tyr Pro Ser Gly Tyr Glu Asn Pro
65                  70                  75                  80

Phe Leu His Ala Ile Asn Asn Gly Gly Tyr Thr Asn Thr Arg Ile Glu
```

-continued

```
                85                  90                  95
Lys Tyr Glu Asp Gly Gly Val Leu His Val Ser Phe Ser Tyr Arg Tyr
            100                 105                 110

Glu Ala Gly Arg Val Ile Gly Asp Phe Lys Val Val Gly Thr Gly Phe
        115                 120                 125

Pro Glu Asp Ser Val Ile Phe Thr Asp Lys Ile Ile Arg Ser Asn Ala
    130                 135                 140

Thr Val Glu His Leu His Pro Met Gly Asp Asn Val Leu Val Gly Ser
145                 150                 155                 160

Phe Ala Arg Thr Phe Ser Leu Arg Asp Gly Gly Tyr Tyr Ser Phe Val
                165                 170                 175

Val Asp Ser His Met His Phe Lys Ser Ala Ile His Pro Ser Ile Leu
            180                 185                 190

Gln Asn Gly Gly Pro Met Phe Ala Phe Arg Arg Val Glu Glu Leu His
        195                 200                 205

Ser Asn Thr Glu Leu Gly Ile Val Glu Tyr Gln His Ala Phe Lys Thr
    210                 215                 220

Pro Ile Ala Phe Ala Arg Ser Arg Ala Gln Ala Ser Asn Ser Ala Val
225                 230                 235                 240

Asp Gly Thr Ala Gly Pro Gly Ser Ala Ala Thr Leu Asp His Asn Gln
                245                 250                 255

Pro Tyr His Ile Cys Arg Gly Phe Thr Cys Phe Lys Lys Pro Pro Thr
            260                 265                 270

Pro Pro Pro Glu Pro Glu Thr
        275

<210> SEQ ID NO 29
<211> LENGTH: 238
<212> TYPE: PRT
<213> ORGANISM: Aequorea Victoria

<400> SEQUENCE: 29

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175
```

-continued

```
Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 30
<211> LENGTH: 225
<212> TYPE: PRT
<213> ORGANISM: Discosoma sp.

<400> SEQUENCE: 30

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225
```